US011351257B2

(12) United States Patent
Neri et al.

(10) Patent No.: US 11,351,257 B2
(45) Date of Patent: Jun. 7, 2022

(54) ANTIBODY COMPOSITIONS

(71) Applicant: Philogen S.p.A., Siena (IT)

(72) Inventors: Giovanni Neri, Siena (IT); Camilla Bacci, Monteriggioni (IT)

(73) Assignee: PHILOGEN S.P.A., Siena (IT)

( * ) Notice: Subject to any disclaimer, the term of this patent is extended or adjusted under 35 U.S.C. 154(b) by 402 days.

(21) Appl. No.: 16/317,902

(22) PCT Filed: Jul. 14, 2017

(86) PCT No.: PCT/EP2017/067870
§ 371 (c)(1),
(2) Date: Jan. 15, 2019

(87) PCT Pub. No.: WO2018/011404
PCT Pub. Date: Jan. 18, 2018

(65) Prior Publication Data
US 2021/0093720 A1 Apr. 1, 2021

(30) Foreign Application Priority Data
Jul. 15, 2016 (GB) ..................................... 1612317

(51) Int. Cl.
| A61K 39/395 | (2006.01) |
| A61K 9/00 | (2006.01) |
| A61K 31/704 | (2006.01) |
| A61K 38/19 | (2006.01) |
| A61K 38/20 | (2006.01) |
| A61K 47/02 | (2006.01) |
| A61K 47/18 | (2017.01) |
| A61K 47/26 | (2006.01) |

(52) U.S. Cl.
CPC ...... *A61K 39/39591* (2013.01); *A61K 9/0019* (2013.01); *A61K 31/704* (2013.01); *A61K 38/191* (2013.01); *A61K 38/2013* (2013.01); *A61K 39/3955* (2013.01); *A61K 47/02* (2013.01); *A61K 47/183* (2013.01); *A61K 47/26* (2013.01)

(58) Field of Classification Search
CPC ............ A61K 39/39591; A61K 9/0019; A61K 31/704; A61K 38/191; A61K 38/2013; A61K 39/3955; A61K 47/02; A61K 47/183; A61K 47/26
See application file for complete search history.

(56) References Cited

U.S. PATENT DOCUMENTS

| 4,457,916 | A | 7/1984 | Hayashi et al. | |
| 8,784,824 | B2* | 7/2014 | Zardi | C07K 14/57 424/178.1 |
| 9,902,779 | B2* | 2/2018 | Yu | C07K 16/30 |
| 10,195,253 | B2 | 2/2019 | Schwager | |
| 2007/0293432 | A1* | 12/2007 | Furfine | C07K 14/4705 514/8.1 |
| 2008/0311119 | A1 | 12/2008 | Maloney | |
| 2010/0209434 | A1* | 8/2010 | Bishop | A61P 1/04 424/158.1 |
| 2014/0219920 | A1* | 8/2014 | Schwagen | A61K 38/191 424/9.1 |
| 2016/0106844 | A1* | 4/2016 | Bañado | A61K 47/26 424/134.1 |

FOREIGN PATENT DOCUMENTS

| WO | 1999058570 A2 | 11/1999 |
| WO | 2001062298 A3 | 8/2001 |
| WO | 2007128563 A1 | 11/2007 |
| WO | 2007149334 A2 | 12/2007 |
| WO | 2013045125 A1 | 4/2013 |
| WO | 2015157286 A1 | 10/2015 |
| WO | 2016180715 A1 | 11/2016 |

OTHER PUBLICATIONS

Papadia et al. "Isolated limb perfusion with the tumor-targeting human monoclonal antibody-cytokine fusion protein L19-TNF plus melphalan and mild hyperthermia in patients with locally advanced extremity melanoma: L19-TNF ILP in Extremity Melanoma", J. Sur. Onco., vol. 107, No. 2, pp. 171-179 (Year: 2012).*
Wang et al. "Antibody Structure, Instability, and Formulation", J Pharm Sci. Jan. 2007;96(1):1-26. (Year: 2007).*
Blick et al., "Phase I Study of Recombinant Tumor Necrosis Factor In Cancer Patients", Cancer Research, vol. 47, Jun. 1, 1987, pp. 2986-2989.
Boyd et al., "Intra-Lesional Interleukin-2 for the Treatment of in-Transit Melanoma", Journal of Surgical Oncology, vol. 104, Dec. 2011, pp. 711-717.
Carnemolla et al., "Enhancement of the Antitumor Properties of Interleukin-2 by its Targeted Delivery to the Tumor Blood Vessel Extracellular Matrix", Blood, vol. 99, No. 5, Mar. 1, 2002, pp. 1659-1665.
Carswell et al., "An Endotoxin-Induced Serum Factor that Causes Necrosis of Tumors", Proc Natl Acad Sci., vol. 72, No. 9, Sep. 1975, pp. 3666-3670.
Clauss , "A Polypeptide Factor Produced by Fibrosarcoma Cells that Induces Endothelial Tissue Factor and Enhances the Procoagulant Response to Tumor Necrosis Factor/Cachectin", J Biol Chem., vol. 265, No. 12, Apr. 25, 1990, pp. 7078-7083.
Clauss et al., "Vascular Permeability Factor: A Tumor-Derived Polypeptide that Induces Endothelial Cell and Monocyte Procoagulant Activity and Promotes Monocyte Migration", J Exp Med., vol. 172, No. 6, Dec. 1, 1990, pp. 1535-1545.

(Continued)

*Primary Examiner* — Daniel E Kolker
*Assistant Examiner* — Peter Johansen
(74) *Attorney, Agent, or Firm* — Kilpatrick Townsend & Stockton LLP

(57) ABSTRACT

This invention relates to stable formulations that can be prepared to high concentration of active agent using low amounts of detergents and to methods for producing such formulations. In particular, this invention relates to formulations containing the L19-TNFα immunocytokine.

22 Claims, 8 Drawing Sheets

Specification includes a Sequence Listing.

(56) References Cited

OTHER PUBLICATIONS

Danielli et al., "A Phase II Study of Intratumoral Application of L19IL2/L19TNF in Melanoma Patients in Clinical Stage III or Stage IV M1a with Presence of Injectable Cutaneous and/or Subcutaneous Lesions", Journal of Clinical Oncology, vol. 32, No. 5, May 2014, 2 pages.
Danielli et al., "Intralesional administration of L19-IL2/U9-TNF in stage III or stage IVM1a Melanoma Patients Results of a Phase II Study", Cancer Immunol Immunother., vol. 64, No. 8, Aug. 2015, pp. 999-1009.
Dehesa et al., "Experience in the Treatment of Cutaneous in-Transit Melanoma Metastases and Satellitosis with Intralesional Interleukin-2", Actas Dermosifiliogr., vol. 100, No. 7, Sep. 2009, pp. 571-585.
Fraker et al., "Isolated Limb Perfusion with High-Dose Tumor Necrosis Factor For Extremity Melanoma and Sarcoma", Important Advances in Oncology, 1994, pp. 179-192.
British Patent Application No. 1612317.6 , Search Report, dated Apr. 18, 2017, 6 pages.
Gutwald et al., "Peritumoral Injections of Interleukin 2 Induce Tumour Regression in Metastatic Malignant Melanoma", British Journal of Dermatology., vol. 130, No. 4, Apr. 1994, pp. 541-542.
Helson et al., "Effect of Tumour Necrosis Factor on Cultured Human Melanoma Cells", Nature, vol. 258, No. 5537, Dec. 25, 1975, pp. 731-732.
Kubo et al., "Interferon-Beta Therapy for Malignant Melanoma: The Dose is Crucial for Inhibition of Proliferation and Induction of Apoptosis of Melanoma Cells", Archives of Dermatological Research, vol. 300, No. 6, Jul. 2008, pp. 297-301.
Palladino et al., "Characterization of the Antitumor Activities of Human Tumor Necrosis Factor-Alpha and the Comparison with other Cytokines: Induction of Tumor-Specific Immunity", The Journal of Immunology., vol. 138, No. 11, Jun. 1, 1987, pp. 4023-4032.
Papadia et al., "Isolated Limb Perfusion with the Tumor-Targeting Human Monoclonal Antibody-Cytokine Fusion Protein L19-TNF Plus Melphalan and Mild Hyperthermia in Patients with Locally Advanced Extremity Melanoma", Journal of Surgical Oncology, vol. 107, No. 2, Feb. 2013, pp. 173-179.
Pasche et al., "Immunocytokines: A Novel Class of Potent Armed Antibodies", Drug Discovery Today, vol. 17, No. 11-12, Jun. 17, 2012, pp. 583-590.
PCT Patent Application No. PCT/EP2017/067870, International Preliminary Report on Patentability, dated Oct. 8, 2018, 17 pages.
PCT Patent Application No. PCT/EP2017/067870, International Search Report and Written Opinion, dated Nov. 3, 2017, 15 pages.
Pretto et al., "Preclinical Evaluation of IL2-based Immunocytokines Supports their use in Combination with Dacarbazine, Paclitaxel and TNF-based Immunotherapy", Cancer Immunol Immunother., vol. 63, No. 9, Sep. 2014, pp. 901-910.
Radny et al., "Phase II Trial of Intralesional Therapy with Interleukin-2 in Soft-Tissue Melanoma Metastases", British Journal of Cancer, vol. 89, No. 9, Nov. 3, 2003, pp. 1620-1626.
Schwager et al., "The Immunocytokine L19-IL2 Eradicates Cancer When Used in Combination with CTLA-4 Blockade or with L19-TNF", Journal of Investigative Dermatology, vol. 133, No. 3, Mar. 2013, pp. 751-758.
Si et al., "Clinical Responses and Lymphoid Infiltrates in Metastatic Melanoma Following Treatment with Intralesional GM-CSF", Melanoma Research, vol. 6, No. 3, Jun. 1996, pp. 247-255.
Singh et al., "Effect of Polysorbate 80 Quality on Photostability of a Monoclonal Antibody", AAPS PharmSciTech., vol. 13, No. 2, Jun. 2012, pp. 422-430.
Tartaglia et al., "Ligand Passing: The 75-kDa Tumor Necrosis Factor (TNF) Receptor Recruits TNF for Signaling by the 55-kDa TNF Receptor", The Journal of Biological Chemistry, vol. 268, No. 25, Sep. 5, 1993, pp. 18542-18548.
Testori et al., "Local and Intralesional Therapy of in-Transit Melanoma Metastases", Journal of Surgical Oncology, vol. 104, Sep. 2011, pp. 391-396.
Weide et al., "High Response Rate After Intratumoral Treatment with Interleukin-2: Results from a Phase 2 Study in 51 Patients with Metastasized Melanoma", Cancer., vol. 116, No. 17, Sep. 1, 2010, pp. 4139-4146.
Weide et al., "Intralesional Treatment of Metastatic Melanoma: a Review of Therapeutic Options", Cancer Immunology, Immunotherapy, vol. 66, No. 5, May 2017, pp. 647-656.
Weide et al., "Intralesional Treatment of Stage III Metastatic Melanoma Patients with L19-IL2 Results in Sustained Clinical and Systemic Immunologic Responses", Cancer Immunol Res., vol. 2, No. 7, Jul. 2014, pp. 668-678.
Wussow et al., "Intralesional Interferon-Alpha Therapy in Advanced Malignant Melanoma", Cancer, vol. 61, Mar. 1988, pp. 1071-1074.
Zbacnik et al., "Role of Buffers in Protein Formulations", Journal of Pharmaceutical Sciences., vol. 106, 2017, pp. 713-733.
European Patent Application No. EP17745672.0, Examination Report dated Jan. 27, 2021, 5 pages.
Chang et al., "Advances and Challenges in Developing Cytokine Fusion Proteins as Improved Therapeutics", Expert Opinion on Drug Discovery, 4:181-193, Feb. 2, 2009, 15 pages.
Schmidt, "Fusion Proteins: Applications and Challenges", Chapter 1 of Fusion Protein Technologies for Biopharmaceuticals: Applications and Challenges, First Edition, 2013, 25 pages.

\* cited by examiner

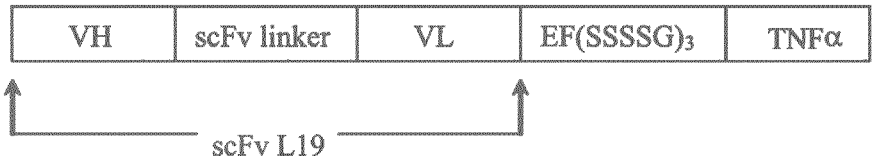

L19TNFα

L19-VH

CDR1             CDR2
EVQLLESGGGLVQPGGSLRLSCAASGFTFSSFSMSWVRQAPGKGLEWVSSISGSSGTTYYADSVKGRF

CDR3
TISRDNSKNTLYLQMNSLRAEDTAVYYCAKPFPYFDYWGQGTLVTVSS scFV LINKER
GDGSSGGSGGAS

L19-VL

CDR1             CDR2
EIVLTQSPGTLSLSPGERATLSCRASQSVSSSFLAWYQQKPGQAPRLLIYYASSRATGIPDRFSGSGS

CDR3
GTDFTLTISRLEPEDFAVYYCQQTGRIPPTFGQGTKVEIK

LINKER
EFSSSSGSSSSGSSSSG hTNFα
VRSSSRTPSDKPVAHVVANPQAEGQLQWLNRRANALLANGVELRDNQLVVPSEGLYLIYSQVLFKGQG
CPSTHVLLTHTISRIAVSYQTKVNLLSAIKSPCQRETPEGAEAKPWYEPIYLGGVFQLEKGDRLSAEI
NRPDYLDFAESGQVYFGIIAL

Figure 1

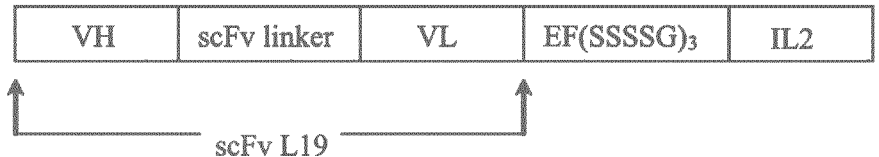

L19IL2

L19-VH

```
                              CDR1                           CDR2
EVQLLESGGGLVQPGGSLRLSCAASGFTFSSFSMSWVRQAPGKGLEWVSSISGSSGTTYYADSVKGRF
                              CDR3
TISRDNSKNTLYLQMNSLRAEDTAVYYCAKPFPYFDYWGQGTLVTVSS
``` scFv LINKER
GDGSSGGSGGAS

L19-VL

```
                           CDR1                      CDR2
EIVLTQSPGTLSLSPGERATLSCRASQSVSSSFLAWYQQKPGQAPRLLIYYASSRATGIPDRFSGSGS
                  CDR3
GTDFTLTISRLEPEDFAVYYCQQTGRIPPTFGQGTKVEIK
```

LINKER
EFSSSSGSSSSGSSSSG hIL2
APTSSSTKKTQLQLEHLLLDLQMILNGINNYKNPKLTRMLTFKFYMPKKATELKHLQCLEEELKPLEE
VLNLAQSKNFHLRPRDLISNINVIVLELKGSETTFMCEYADETATIVEFLNRWITFCQSIISTLT

Figure 2

Baseline
After 2 cycles
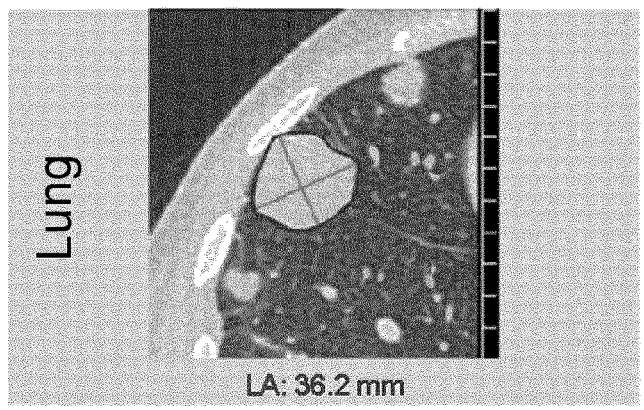
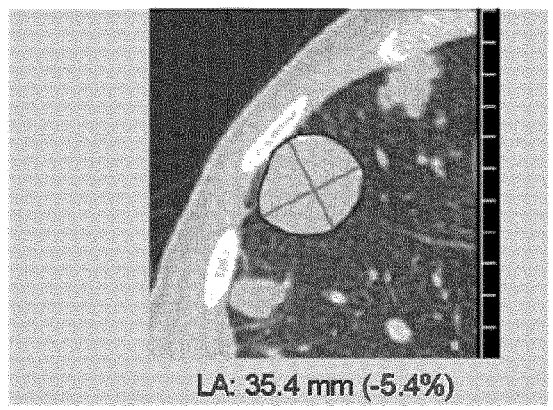
Figure 8

ANTIBODY COMPOSITIONS

FIELD OF THE INVENTION

This invention relates to stable formulations that can be prepared to high concentration of active agent using low amounts of detergents and to methods for producing such formulations. In particular, this invention relates to formulations containing the L19-TNFα immunocytokine.

BACKGROUND OF THE INVENTION

Most proteins tend to aggregate and form precipitate as the concentration of the protein increases. The protein concentration at which aggregation and precipitation occurs varies from protein to protein. While protein aggregation and/or precipitation substantially reduces the efficacy of therapeutic proteins, many protein-based therapies require high-concentration protein formulations for delivery to the patient. Thus, for some protein therapies, therapeutic efficacy is limited because high-concentration formulations cannot be produced or cannot be stored for a useful length of time due to protein aggregation and/or precipitation. This can be a problem with protein formulations for local administration because often only small volumes can be delivered. Furthermore, a formulation enabling a higher concentration of protein means that less vials are needed per each cycle of treatment. A smaller number of vials facilitates the management of the lots produced, including easier shipment and storage conditions. This is a particularly valuable feature, when the vials must be stored at −80° as in the case of L19-TNFα.

Polysorbate

Polysorbates are surfactants that are produced by reacting the polyol, sorbitol, with ethylene oxide. The number in the name of the Polysorbate indicates the average number of moles of ethylene oxide that has been reacted per mole of sorbitol. The polyoxyethylenated sorbitan is then reacted with fatty acids obtained from vegetable fats and oils such as lauric acid, palmitic acid, stearic acid and oleic acid. Polysorbates such as polysorbate20 and polysorbate80 are commercially available.

Polysorbates help other ingredients to dissolve in a solvent in which they would not normally dissolve. They also help to form emulsions by reducing the surface tension of the substances to be emulsified.

Hence, polysorbate, e.g. that sold under the registered trade mark "Tween", can be used to stabilize therapeutic proteins for injection because it is non-pyrogenic, non-hemolytic and only slightly irritant. It can increase solubilization by preventing the non-specific binding that leads to aggregation and/or precipitation. Higher concentrations of polysorbate generally result in greater stability of the protein solution. Polysorbates may however be toxic. On repeated intravenous administration, effects on the liver, spleen and kidneys were seen in baby animals exposed to polysorbate80:polysorbate20 mixture, some fatalities occurred. In rats and hamsters, repeated oral exposure to polysorbate20 produced damage at a range of sites including the gastrointestinal tract, liver and kidneys. Pharmaceutical formulations should therefore limit, as far as possible, the use of polysorbates for parenteral administration.

Therapeutic Approaches Against Melanoma

In patients with locally advanced melanoma, i.e., stage IIIB/C or stage IVM1a, intralesional injection of accessible metastases has been shown to represent an attractive therapeutic avenue with distinctive advantages over other approaches (1).

Agents, which have been investigated for the intralesional treatment of melanoma, include bacille Calmette-Guerin (BCG) and cytokines like granulocyte-macrophage colony stimulating factor (GM-CSF) (2), interferon (TNF)-α (3) and -β (4) and interleukin 2 (IL2) (5-9). In some studies, 72 melanoma patients in stages IIIB, IIIC and IVM1a received intratumoral injections of the cytokine three times weekly, with a maximum daily dose of 16 million international units (MIU) of recombinant interleukin-2 (IL2—Proleukin™) or variable, according to the individual tumor burden of patients (6, 7). New lesions appearing during treatment were also injected and treatment was continued until all lesions, including those that appeared during treatment, finally regressed.

Tumor Necrosis Factor α (TNFα) is a cytokine produced by many cell types, mainly activated monocytes and macrophages. It is expressed as a 26 kDa integral transmembrane precursor protein from which a mature protein of approximately 17 kDa is released by proteolytic cleavage. The soluble bioactive TNFα is a homotrimer that interacts with two different cell surface receptors (10) p55TNFR (50-60 kDa) and p75TNFR (75-80 kDa).

TNFα can induce hemorrhagic necrosis of transplanted solid tumors, in vivo (11), and can exert cytotoxic activity in vitro against some tumor cell lines (12).

The anti-tumor efficiency of TNFα in some animal models fostered hopes of its possible use as a therapeutic agent in human cancer. Clinical trials performed to demonstrate the anti-tumor efficacy of TNFα, however, showed that systemically administered therapeutically effective doses were accompanied by unacceptably high levels of systemic toxicity, hypotension being the most common dose-limiting toxic effect. Moreover, TNFα has a very rapid clearance from the bloodstream (plasma half-life generally less than 30 minutes) (13), which decreases the hematic concentration under therapeutic levels, very rapidly. Good clinical results have been achieved in humans only in loco-regional treatments of non-disseminated tumors (e.g., isolated-limb-perfusion for sarcoma and melanoma) (14).

The anti-tumour activity of TNFα in many animal models seems to be due to a combination of a direct toxic effect (in a combination with tumor-derived factors that synergise with TNFα) on endothelial cells of the growing tumor vasculature (15), as well as to alterations of the hemostatic properties of proliferating endothelial cells in tumor angiogenesis (16). There is also evidence of a direct cytotoxic effect on tumor cells. Indirect (host-mediated) effects of TNFα, such as the induction of T cell-dependent immunity, can contribute to tumor regression on animal models (17).

In contrast to systemic treatment, the local application of drugs results in higher concentration at the site of disease, leading to an improved therapeutic outcome with fewer systemic side effects. In contrast to surgery, which is normally limited to a few operable lesions, intralesional interventional procedures may allow the treatment of diffuse metastatic spread distributed over large anatomical regions.

Immunocytokines

Immunocytokines are recombinant fusion proteins in which cytokines of interest are fused C- or N-terminally to antibody fragments, which act as delivery/targeting vehicles. The antibody moiety favours preferential accumulation and prolonged residence in regions in which the antibody's cognate antigen is at high concentration. The antibody domain is therefore selected to bind antigens that are prevalent at the site of disease, thus leading to an improved therapeutic activity while sparing normal organs (18).

L19-TNFα, also known as "FIBROMUN", is an immunocytokine, consisting of three polypeptides each of which is composed of human TNFα (hTNFα) fused at its N-terminus, via a linker, to the C-terminus of recombinant monoclonal antibody L19 (FIG. 1). In this fusion, L19 is an antibody molecule in the scFV format, which recognizes the alternatively spliced extra-domain B (EDB) of fibronectin (FN), a marker of tumor angiogenesis (19). The soluble TNFα domain homotrimerises, hence L19-TNFα itself is a trimer comprising three L19 scFV domains. The amino acid sequence of each L19-TNFα polypeptide is set out in SEQ ID NO: 1.

EDB-containing FN is present in the newly formed vasculature of most solid tumors and hematological malignancies (20) but absent from almost all healthy adult tissues (with the exception of tissues of the female reproductive cycle). The construction of L19-TNFα is disclosed in WO01/062298 (21). Using immunohistochemistry, the L19-TNFα fusion protein was shown to strongly stain blood vessels of glioblastoma tumor. Substantial quantities of L19-TNFα remain in the tumour hours and even days after intratumoural administration. The localisation of L19-TNFα fusion protein in the tumoral neovasculature was confirmed by microradiographic analysis. Accumulation of the radiolabeled fusion protein was shown in the blood vessels of the F9 mouse tumor. No accumulation of radiolabeled fusion protein was detected in the vessels of the other organs of tumor bearing mice.

L19-IL2, also known as "DARLEUKIN" is an immunocytokine, consisting of human IL2 fused at its N-terminus, via a linker, to the C-terminus of recombinant monoclonal antibody L19 (FIG. 2 and (21)). In this construct, L19 is an antibody in the scFV format, which recognizes EDB, as discussed above. Dimerisation via the IL2 domain results in the formation of L19-IL2 homodimers. The amino acid sequence of each L19-IL2 polypeptide is set out in SEQ ID NO: 2.

Targeted forms of IL2 injected intralesionally into melanoma metastases exhibits a prolonged residence time in the lesions, as compared to the untargeted form, therefore allowing an extended immunological action, reduction in the frequency of administrations and a shorter duration of the treatment (22). Preliminary clinical data showed that this approach is efficient in regional control of disease progression, increased time to distant metastasis and evidence of effect on circulating immune cell populations (23).

Furthermore, preclinical data (24) have shown that a combination of L19-IL2 with L19-TNFα in a syngeneic immunocompetent mouse model of cancer induced complete remissions when administered as a single intratumoral injection, whereas the two components did not lead to curative remission when administered separately (25).

Formulations of L19 immunocytokines are disclosed in WO2007/128563 (27). However, no successful approach for formulating high-concentration L19-TNFα formulations has been disclosed or even suggested, before the instant disclosure.

SUMMARY OF THE INVENTION

Disclosed here are buffer compositions which enable L19-TNFα to be formulated at concentrations of 0.2 mg/mL or more. Surprisingly, the stability of L19-TNFα formulations at these concentrations was found to be possible only using phosphate buffer or hepes buffer but not in other types of buffer. Furthermore, the stability of L19-TNFα formulations was found to be unexpectedly sensitive to the amount of detergent, specifically polysorbate. Only in the phosphate buffer compositions of the invention could L19-TNFα be formulated with low amount of polysorbate (but not in Hepes buffers).

In the phosphate buffers of the invention, a concentration of about 0.01-0.03% (v/v) polysorbate is particularly good, and remarkably low considering the 0.1%-0.2% found to be optimal for solution stability in hepes buffer formulations such as Hepes-7, Hepes-8 and Hepes-9, discussed below. Surprisingly, it is demonstrated herein that a polysorbate20 concentration as low as 0.01% (v/v) was able to maintain soluble L19-TNFα in phosphate buffers.

The maximum concentration of Tween/polysorbate recommended for human use is 0.1%. There are several forms of Tween/polysorbate such as Tween/polysorbate-20, Tween/polysorbate40, Tween/polysorbate-60 and Tween/polysorbate-80.

The invention provides buffers which are suitable for injection into a subject, and suitable for dissolving the L19-TNFα immunocytokine at a concentration of at least 0.2 mg/mL.

In one aspect, a composition is provided comprising L19-TNFα as set forth in SEQ ID NO: 1, dissolved in a sodium phosphate buffer which comprises a salt at a concentration of at least about 1.5 mM, polysorbate at a concentration of at least about 0.005% (v/v), and a stabilizer, wherein the pH of the sodium phosphate buffer is higher than 7.5 and lower than 9. As disclosed herein, this buffer composition enables the L19-TNFα immunocytokine to be dissolved at a concentration of over 0.2 mg/mL. Hence, in some embodiments, the concentration of the L19-TNFα immunocytokine is at least about 0.2 mg/mL.

Also provided is a composition is provided comprising L19-TNFα as set forth in SEQ ID NO: 1, dissolved in a sodium phosphate buffer which comprises a salt at a concentration of at least 1.5 mM, polysorbate at a concentration of at least 0.005% (v/v), and a stabilizer, wherein the pH of the sodium phosphate buffer is higher than 7.5 and lower than 9. As disclosed herein, this buffer composition enables the L19-TNFα immunocytokine to be dissolved at a concentration of over 0.2 mg/mL. Hence, in some embodiments, the concentration of the L19-TNFα immunocytokine is at least 0.2 mg/mL.

In some embodiments, the pH of the composition may be within a range as set out here, or about such a range: 7.6-8.9 or 7.7-8.8, more preferably 7.8-8.8, or 8.5 or about 8.5. Most preferably, the pH of the composition is 8, or about 8.

Also provided is a composition comprising the L19-TNFα immunocytokine as set forth in SEQ ID NO:1, dissolved in a sodium phosphate buffer which comprises NaCl at a concentration of 5-50 mM, polysorbate at a concentration of 0.005-0.03% (v/v), and a stabilizer, wherein the pH of the sodium phosphate buffer is 7.5-8.5, and wherein the concentration of the L19-TNFα immunocytokine is at least 0.2 mg/mL.

Also provided is a composition comprising the L19-TNFα immunocytokine as set forth in SEQ ID NO:1, dissolved in a sodium phosphate buffer which comprises NaCl at a concentration of about 5-50 mM, polysorbate at a concentration of about 0.005-0.03% (v/v), and a stabilizer, wherein the pH of the sodium phosphate buffer is about 7.5-8.5, and wherein the concentration of the L19-TNFα immunocytokine is at least about 0.2 mg/mL.

In any of the compositions disclosed herein, polysorbate may be present at a concentration within a range as set out here (presented as v/v), or about such a range: 0.005-0.03%, 0.008-0.03% or 0.01-0.03%, or 0.005-0.1% or more preferably 0.01-0.02%. Most preferably, polysorbate is present at 0.01%, or about 0.01%, (v/v). In some embodiments, the polysorbate concentration may be slightly higher, e.g. up to a maximum concentration of 0.04% (v/v), about 0.04% (v/v), 0.05% (v/v), about 0.05% (v/v), 0.06% (v/v), about 0.06% (v/v), 0.07% (v/v), about 0.07% (v/v), about 0.07% (v/v), 0.08% (v/v), about 0.08% (v/v), 0.09% (v/v), about 0.09% (v/v), 0.1% (v/v) or about 0.1% (v/v). The polysorbate may be polysorbate20 or polysorbate 80. Preferably the polysorbate is polysorbate20. A salt is used to maintain the isotonicity. The skilled person will appreciate that the salt should be a pharmaceutically acceptable salt. The salt is preferably sodium chloride, although other salts such as potassium chloride, magnesium sulphate, magnesium chloride, calcium chloride, or calcium phosphate can also be used. The salt may be present at a concentration within a range as set out here, or about such a range: 1-100 mM, 1.5-90 mM, 2-80 mM, 5-75 mM, 10-50 mM, preferably 10-40 mM, more preferably 20-30 mM. In some embodiments, the salt is present at 30 mM or at about 30 mM. In preferred embodiments, the salt is NaCl and/or KCl.

In some embodiments, the salt is NaCl. NaCl may be present at a concentration within a range as set out here, or about such a range: 10-50 mM, preferably 10-40 mM, more preferably 20-30 mM. Most preferably, NaCl is present at 30 mM or at about 30 mM.

In some embodiments, the salt is KCl. KCl may be present at a concentration within a range as set out here, or about such a range: 1-50 mM, 1.5-40 mM, 1.5-30 mM, 1.5-20 mM or 1.5-10 mM.

A stabilizer is used to stabilize the protein in its native conformation. Suitable stabilizers for protein solutions are well known in the art. The stabilizer may be a sugar. The stabilizer can be selected from the group consisting of mannitol, trehalose, sucrose, sorbitol, maltose and xylitol. The results provided herein show that different types of stabilizer are effective. The stabilizer (e.g. a sugar) may be present at a concentration within a range as set out here, or about such a range: 10-500 mM, 20-400 mM, 30-300 mM, 40-200 mM, 50-185 mM, 55-100 mM, 60-90 mM, or more preferably 65-85 mM.

Most preferably the stabilizer is mannitol. Mannitol may be present at a concentration within a range as set out here, or about such a range: 20-200 mM, 30-150 mM, 50-100 mM, 60-90 mM, or more preferably 65-85 mM. Most preferably, mannitol is present at 75 mM or at about 75 mM.

The L19-TNFα immunocytokine may be present at a concentration as set out here, or about such a concentration: at least 0.3 mg/mL, at least 0.4 mg/mL, at least 0.5 mg/mL, at least 0.6 mg/mL or at least 0.8 mg/mL. Preferably, the L19-TNFα immunocytokine is present at 0.45 mg/mL or about 0.45 mg/mL, although higher concentrations also may be preferred in some embodiments. The L19-TNFα immunocytokine may be present at a concentration within a range as set out here, or about such a range: 0.1-2.0 mg/mL, 0.2-1.5 mg/mL, 0.3-1.0 mg/mL, 0.4-0.8 mg/mL or 0.4-0.6 mg/mL.

The polysorbate may be polysorbate20. In some embodiments, the pH of the composition may be within a range as set out here, or about such a range: 7.6-8.4 or 7.7-8.3, more preferably 7.8-8.8, 7.8-8.2 or 7.9-8.1. Most preferably, the pH of the composition is 8, or about 8.

The sodium phosphate buffer may comprise glycerol. Glycerol may be present at a concentration within a range as set out here (presented as w/v), or about such a range: 0.1-2%, preferably 0.3-1.8%, more preferably 0.5-1.7%, 0.5-1.5%, 1-1.5%, 1-1.2%. Most preferably, the sodium phosphate buffer comprises glycerol at a concentration of 1% w/v or about 1% w/v.

The sodium phosphate may comprise EDTA. EDTA may be present at a concentration within a range set out here, or about such range: 1-20 mM, preferably 2-15 mM, or more preferably 3-10 mM or 6-9 mM. Most preferably the sodium phosphate buffer comprises EDTA is present at 5 mM or at about 5 mM. However, EDTA is not needed for the stability of the formulation itself, but is useful as a preservative.

The sodium phosphate buffer may comprise $NaH_2PO_4$. $NaH_2PO_4$ may be present at a concentration within a range as set out here, or about such a range: 1-100 mM, preferably 2-50 mM, 3-30 mM, 5-25 mM, 8-23 mM, 10-20 mM, or more preferably 12-18 mM. Most preferably, $NaH_2PO_4$ is present at a concentration of 15 mM or about 15 mM. The sodium phosphate buffer may comprise $Na_2HPO_4$. $Na_2HPO_4$ may be present in a concentration within a range as set out here, or about such a range: 1-100 mM, preferably 2-50 mM, 3-30 mM, 4-25 mM, 5-20 mM, 6-18 mM, or more preferably 7-15 mM. Most preferably $Na_2HPO_4$ is present at a concentration of 10 mM or 10 mM.

In some embodiments, the sodium phosphate buffer may comprise KCl. KCl may be present in a concentration within a range as set out here, or about such a range: 0.1-10 mM, 0.2-5 mM, 0.5-3 mM, preferably 1-2 mM, more preferably 1.1-1.9, 1.2-1.9, 1.3-1.8, 1.4-1.7 mM or 1.4-1.6. In some embodiments, KCl is absent. However, in some embodiments (particularly when other salts are not present), KCl can be present at a much higher concentration, for instance up to 5 mM or about 5 mM, 10 mM or about 10 mM, 20 mM or about 20 mM, 30 mM or about 30 mM, 40 mM or about 40 mM, 50 mM or about 50 mM, 100 mM or about 100 mM. Most preferably, the sodium phosphate buffer comprises KCl at a concentration of 1.5 mM or about 1.5 mM.

Advantageously, the sodium phosphate buffer comprises 15 mM $NaH_2PO_4$ and 10 mM $Na_2HPO_4$ at pH 8.0, 75 mM mannitol, 1% glycerol (w/v), 1.5 mM KCl, 30 mM NaCl and 0.01% polysorbate20. Advantageously, the L19-TNFα immunocytokine concentration is at least 0.4 mg/mL.

Also preferred are sodium phosphate buffers comprising about 15 mM $NaH_2PO_4$ and about 10 mM $Na_2HPO_4$ at pH 8.0, about 75 mM mannitol, about 1% glycerol (w/v), about 1.5 mM KCl, about 30 mM NaCl and about 0.01% polysorbate20. Advantageously, the L19-TNFα immunocytokine concentration is at least about 0.4 mg/mL.

Also advantageously, the sodium phosphate buffer comprises 15 mM $NaH_2PO_4$ and 10 mM $Na_2HPO_4$ at pH 8.0, 75 mM mannitol, 1% glycerol (w/v), 1.5 mM KCl, 30 mM NaCl, 0.01% polysorbate20 and 5 mM EDTA. Advantageously, the L19-TNFα immunocytokine concentration is at least 0.4 mg/mL.

Also preferred are sodium phosphate buffers comprising about 15 mM $NaH_2PO_4$ and about 10 mM $Na_2HPO_4$ at pH 8.0, about 75 mM mannitol, about 1% glycerol (w/v), about 1.5 mM KCl, about 30 mM NaCl, about 0.01% polysorbate20 and about 5 mM EDTA. Advantageously, the L19-TNFα immunocytokine concentration is at least about 0.4 mg/mL.

In another aspect, the compositions disclosed herein are provided for use in a method of treatment of the human or animal body by therapy. Such treatment involves administration of the composition to a human or animal, preferably a human. The treatment may be of a cancer.

Compositions of the invention are particularly suited to use in treatment of sarcomas. Types of sarcoma can include angiosarcoma, chondrosarcoma, Ewing's sarcoma, fibroblastic sarcoma, Kaposi's sarcoma, leiomyosarcoma, liposarcoma, osteosarcoma, rhabdomyosarcoma and soft tissue sarcoma.

In some embodiments, the composition further comprises the L19-IL2 immunocytokine.

Methods of treating cancer are also provided, such methods comprising administering a composition disclosed herein into a tumour or lesion by injection.

The treated cancer may be a primary tumour. The treated cancer may be metastatic a tumour.

Compositions of the invention are particularly suited to use in treatment of skin cancers, e.g. malignant skin tumour, melanoma or carcinoma, since their location is amenable to direct local injection. Other tumours within the body may also be treated, and injections may be guided to tumours within soft tissue or internal organs, e.g. by sonography (26).

Treatment in accordance with the invention may be used in a surgical context, where injection is performed before, during or after tumour surgery.

Advantageously, the L19-IL2 immunocytokine as set forth in SEQ ID NO:2 is also administered to the patient who is treated with the L19-TNFα immunocytokine. When treatment involves administration of the L19-IL2 immunocytokine, the method may also comprise mixing a composition of the first aspect with an L19-IL2 immunocytokine formulation, prior to administration. In other embodiments, as described below, the L19-TNFα and L19-IL2 compositions are administered separately.

The L19-TNFα immunocytokine and the L19-IL2 immunocytokines may be provided as separate formulations to permit either sequential administration (in either order), which includes essentially-simultaneous administration in which the L19-TNFα and L19-IL2 immunocytokines are administered at essentially the same time. For example, the method of treatment may comprise injecting the L19-TNFα formulation and then immediately injecting the L19-IL2 formulation (or vice-versa).

Sequential administration can also be used to administer the second immunocytokine after a period of time following administration of the first immunocytokine. For example, the immunocytokines can be injected within 24 hours, 12 hours, 1 hour, or preferably within 30 minutes of each other. Preferably, the immunocytokines are administered within a few minutes of each other. The two immunocytokines may be injected at the same point in the tumour site, or at different points. A combined injection of both immunocytokines may be administered. It may be preferable to administer a dose in multiple injections, for example to inject multiple locations across the tumour or around the tumour site, or to facilitate administration of a larger total volume of immunocytokine.

The L19-TNFα immunocytokine and the L19-IL2 immunocytokines may be provided as a combined preparation.

Advantageously, the L19-TNFα formulation and the L19-IL2 formulation may be provided as separate formulations but administered simultaneously by a clinician. An L19-TNFα formulation according to the invention may be mixed with an L19-IL2 formulation prior to administration to the patient. The L19-TNFα and L19-IL2 formulations may be mixed less than 1 hour before administration, less than 30 minutes before administration, less than 15 minutes before administration, less than 5 minutes before administration, less than 2 minutes before administration, or less than 1 minute before administration. In another approach, the clinician administers the L19-TNFα formulation and the L19-IL2 formulation at essentially the same time, without prior mixing.

The invention also provides a method of preparing a formulation suitable for use as an injectable anticancer medicine, the method comprising providing a composition according to the invention, and mixing said composition with an L19-IL2 immunocytokine formulation. This method may be performed immediately before the mixture is administered to a patient.

Preferably, the L19-IL2 immunocytokine is formulated in a phosphate buffer comprising $NaH_2PO_4$ at a concentration of 1-50 mM, NaCl at a concentration of 1-50 mM, KCl at a concentration of 1-2 mM, mannitol at a concentration of 50-200 mM, polysorbate80 at a concentration of 0.05-0.2% (v/v), Glycerol at a concentration of 0.5-2% and EDTA at a concentration of 1-20 mM and pH from 5.5-7.0.

The L19-IL2 immunocytokine is also formulated in a phosphate buffer comprising $NaH_2PO_4$ at a concentration of 1-50 mM, NaCl at a concentration of 1-50 mM, KCl at a concentration of 1-2 mM, mannitol at a concentration of 50-200 mM, polysorbate80 at a concentration of 0.05-0.3% (v/v), and Glycerol at a concentration of 0.5-2% and pH from 5.5-7.0. In some embodiments, a polysorbate80 concentration (v/v) of 0.28%, or about 0.28%, is used.

Alternatively, the L19-IL2 immunocytokine may be formulated in a phosphate buffer comprising $NaH_2PO_4$ at a concentration of about 1-50 mM, NaCl at a concentration of about 1-50 mM, KCl at a concentration of about 1-2 mM, mannitol at a concentration of about 50-200 mM, polysorbate80 at a concentration of about 0.05-0.2% (v/v), Glycerol at a concentration of about 0.5-2% and EDTA at a concentration of about 1-20 mM and pH from about 5.5-7.0.

Alternatively, the L19-IL2 immunocytokine may also be formulated in a phosphate buffer comprising $NaH_2PO_4$ at a concentration of about 1-50 mM, NaCl at a concentration of about 1-50 mM, KCl at a concentration of about 1-2 mM, mannitol at a concentration of about 50-200 mM, polysorbate80 at a concentration of about 0.05-0.3% (v/v), and Glycerol at a concentration of about 0.5-2% and pH from about 5.5-7.0.

The $NaH_2PO_4$ may be present at a concentration within a range as set out here, or about such a range: 2-25 mM, 3-20 mM, more preferably 5-15 mM. Most preferably the $NaH_2PO_4$ is present at 6.7 mM or about 6.7 mM. The NaCl may be present at a concentration within a range as set out here, or about such a range: 5-40 mM or 10-30 mM or more preferably 15-25 mM. Most preferably NaCl is present at 20 mM or about 20 mM. The KCl may be present at a concentration within a range as set out here, or about such a range: 1.2-2.0 mM, more preferably 1.5-1.8 mM. Most preferably, KCl is present at 1.8 mM or about 1.8 mM.

Mannitol may be present at a concentration within a range as set out here, or about such a range: 80-180 mM, or more preferably 100-150 mM. Most preferably, mannitol is present at 133 mM or at about 133 mM. Polysorbate80 may be present at a concentration within a range as set out here (presented as v/v), or about such a range: 0.1-0.3%, 0.07-0.18%, or more preferably 0.08-0.15%. Most preferably, polysorbate80 is present at 0.1% (v/v) or at about 0.1% (v/v).

Glycerol may be present at a concentration within a range as set out here (presented as w/v), or about such a range: 0.7-1.8%, or more preferably 0.8-1.5%. Most preferably, glycerol is present at 1% (w/v) or about 1% (w/v). EDTA may be present at a concentration within a range as set out here, or about such a range: 2-15 mM, or more preferably 3-10 mM or 6-9 mM. Most preferably EDTA is present at 5 mM or at about 5 mM. The pH is preferably 6.0-6.8, more preferably 6.1-6.5 mM or 6.2-6.4. Most preferably, the pH is 6.3 or about 6.3. In a preferred embodiment, EDTA is absent.

Preferably, the L19-IL2 formulation comprises 6.7 mM $NaH_2PO_4$, 20 mM NaCl, 1.8 mM KCl, 133 mM mannitol, 0.1% polysorbate80 (v/v), 1% glycerol (w/v) and 5 mM EDTA and has pH 6.3.

Most preferably, the L19-IL2 formulation comprises 6.7 mM $NaH_2PO_4$, 20 mM NaCl, 1.8 mM KCl, 133 mM mannitol, 0.1-0.3% polysorbate80 (v/v), and 1% glycerol (w/v) and has pH 6.3.

Alternatively, the L19-IL2 formulation comprises about 6.7 mM $NaH_2PO_4$, about 20 mM NaCl, about 1.8 mM KCl, about 133 mM mannitol, about 0.1% polysorbate80 (v/v), about 1% glycerol (w/v) and about 5 mM EDTA and it has pH of about 6.3.

Alternatively, the L19-IL2 formulation comprises about 6.7 mM $NaH_2PO_4$, about 20 mM NaCl, about 1.8 mM KCl, about 133 mM mannitol, about 0.1-0.3% polysorbate80 (v/v), and about 1% glycerol (w/v) and it has pH of about 6.3.

The invention also provides kits. A kit according to the invention may comprise a dry (e.g. lyophilised) preparation of L19-TNFα immunocytokine in a first container, and a buffer solution of the invention as disclosed herein. A kit may further comprise a lyophilised preparation of L19-IL2 immunocytokine in a second container and a second buffer solution as disclosed herein. In some embodiments, the kit may comprise a preparation of the L19-TNFα and/or L19-IL2 immunocytokines in the form of a sterile liquid solution, wherein the immunocytokine is dissolved in a solvent or in an appropriate buffer as described herein. The immunocytokine solutions of the invention are preferably apyrogenic. The skilled person will understand that, when provided separately from a dry or liquid immunoconjugate composition, the buffer will be provided in a separate container.

The kits may include instructions for dissolving the immunocytokines, and/or mixing the immunocytokines, and/or administering the immunocytokines to a cancer patient.

A kit comprising a first container comprising a composition according to the invention is also provided. The kit may contain a second container comprising a preparation of L19-IL2 immunocytokine as discussed. The kits may also include items to aid administration of the immunocytokines to the patient, e.g. syringes and the like.

BRIEF DESCRIPTION OF THE FIGURES

FIG. 1. Schematic structure of the L19-TNFα polypeptide chain (top panel) and amino acid sequence of L19-TNFα (lower panel). (The amino acid sequence of L19-TNFα is set forth in SEQ ID NO:1.)

FIG. 2. Schematic structure of the L19-IL2 polypeptide chain (top panel) and amino acid sequence of L19-IL2 (lower panel). (The amino acid sequence of L19-IL2 is set forth in SEQ ID NO:2.)

FIG. 8. Treatment of a patient with L19-TNFα in phosphate buffer in combination with Doxorubicin. A patient with chondrosarcoma was treated with 2 cycles of L19-TNFα (17 ug/kg-3 weekly injections per cycle) and doxorubicin (60 mg/m² 1 weekly injection per cycle). The target lesion in lung shows growth stabilization at CT after 2 cycles of treatment.

DETAILED DESCRIPTION

Figure 3:
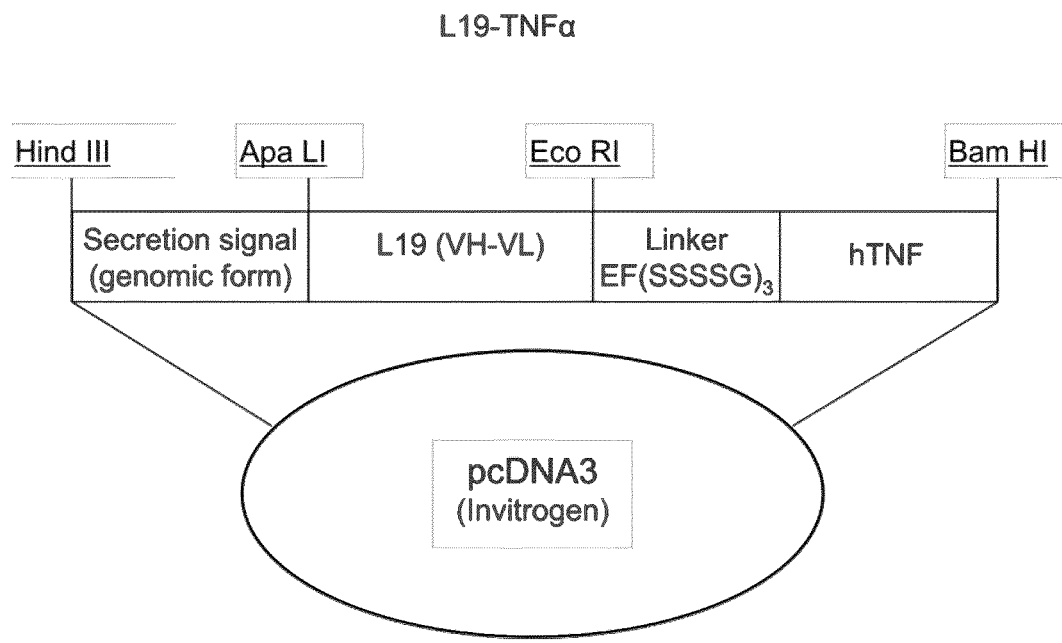
FIG. 3. Diagram of the cloning scheme for L19-TNFα.

The following applications of the present invention are provided by way of example and not limitation.

In some embodiments, the composition of the invention may be administered alone or in combination with other treatments, either simultaneously or sequentially dependent upon the condition to be treated.

Treatments involving the compositions of the invention may include the administration of suitable doses of an anticancer compound. Anti-cancer compounds are cytotoxic compounds which inhibit the growth, division and/or proliferation of cancer cells. Anti-cancer compounds may, in some circumstances, have an effect on normal non-cancer cells in a patient. An anti-cancer compound may, for example, inhibit the cell-cycle or activate apoptosis. Suitable anti-cancer compounds which inhibit the cell cycle include DNA damaging agents and anti-mitotic agents, including inhibitors of mitotic spindle assembly. A DNA damaging agent is a chemotherapeutic compound which induces DNA DSBs in cellular DNA, thereby inhibiting or abolishing DNA replication. Many suitable compounds are known in the art for use in the treatment of cancer, including, for example, bleomycin hydorxyurea, mitomycin and actinomycin and inhibitors of topoisomerase I and II activity, including anthracylines such as daunorubicin, doxorubicin, epirubicin, idarubicin, mitoxantrone and valrubicin, etoposide and teniposide, and members of the tecan family e.g. irinotecan, topotecan, rubitecan. DNA damaging agents may be used as described herein in any convenient form or formulation. For example, any suitable isomer, salt, solvate, chemically protected form, or prodrug of a particular DNA damaging agent may be employed.

In some preferred embodiments, the DNA damaging agent may be doxorubicin ((8S, 10S)-10-(4-amino-5-hydroxy-6-methyl-tetrahydro-2H-pyran-2-yloxy)-6,8,11-trihydroxy-8-(2-hydroxyacetyl)-1-methoxy-7, 8, 9, 10-tetrahydrotetracene-5,12-dione) such as morpholino-doxorubicin, cyanomorpholino-doxorubicin, 2-pyrrolino-doxorubicin and/or deoxydoxorubicin. Doxorubicin is an anthracycline intercalating agent which is widely used in cancer treatment under trade names such as Adriamycin™, and Rubex™.

In some embodiments, the composition of the invention may be administered in combination with doxorubicin.

It is generally convenient to provide the composition of the invention and the doxorubicin as separate molecules.

They may be provided as a combined preparation, or as separate formulations to permit either simultaneous or sequential administration. The clinician can determine the most suitable manner of administering the single dose of each L19-TNFα and doxorubicin to the patient.

For example, the method of treatment may comprise administering the composition of the invention and the doxorubicin in separate injections, simultaneously or sequentially.

Where sequential administration is used, the immunocytokines are preferably administered within 24 hours, 12 hours, 1 hour or more preferably within 30 minutes of each other.

The quantity of L19-TNFα administered will depend on the size and nature of the tumour, among other factors. For example, the dose of L19-TNFα may be in the range of 10-17 μg/kg and the dose of doxorubicin 60 mg/m². The clinician will determine a therapeutically effective amount for administration.

Further treatments may be used in combination with the invention include the administration of suitable doses of pain relief drugs such as non-steroidal anti-inflammatory drugs (e.g. aspirin, paracetamol, ibuprofen or ketoprofen) or opiates such as morphine, or antiemetics. Where the immunocytokines are administered for cancer treatment, they are injected parenterally. In one embodiment, the immunocytokines are injected at the site of the tumour, preferably by intratumoural injection. Peritumoural injection, e.g. local intradermal injection, is another suitable method for administering the immunocytokine locally to a tumour site. In some embodiments, the L19-TNFα immunoconjugate may be administered by infusion, e.g. intravenous/systemic infusion. Embodiments of the invention in which the L19-TNFα immunoconjugate is present at low concentration are particularly suited to administration by infusion.

Treatment of a tumour according to the present invention may include complete eradication of the tumour. The disappearance of any evidence of vital tumour after stopping injections represents complete treatment of the tumour. Disappearance of the tumour may be determined when the tumour has no discernible volume or is no longer visible. Treatment may comprise treatment to eradicate the tumour and prevent tumour regrowth.

Patients are preferably monitored during a follow-up period of at least one month, preferably at least six months or at least a year, after administration of the immunocytokine combination therapy. Disappearance of the tumour, and lack of tumour regrowth, may be observed in the follow-up period. Absence of tumour regrowth may be observed.

The quantity of L19-TNFα and the quantity of L19-IL2 administered will depend on the size and nature of the tumour, among other factors. For example, the dose of L19-TNFα may be in the range of 20 μg-2 mg e.g. 100-1,000 μg, 200-600 μg, or between 300-400 μg. The dose may be 50-500 μg (e.g 100-400 μg) per treatment. The dose of L19-IL2 may be in the range of 1-15 Mio IU (e.g. 10-13 Mio IU) per treatment. The treatment may consist of 13 Mio IU of L19-IL2 and 400 μg of L19-TNF in an approximative volume of 2.0 ml as intratumoral injection. The dose of L19-IL2 may be in the range of 20 μg-3 mg e.g. 100-2,500 μg, 300-2,000 μg or between 500-1,800 μg. These are examples only and, of course, different doses may be used. The formulations of this invention enable larger doses to be administered without a large volume being needed. The clinician will determine a therapeutically effective amount for administration.

The methods may comprise treating a tumour in a patient by injecting L19-TNFα formulation, optionally with the L19-IL2 formulation (administered sequentially or simultaneously) at the tumour site, wherein the tumour disappears in the absence of further doses of the immunocytokine(s). Optionally, further doses may be administered.

In the event of tumour recurrence after the follow-up period, or if other tumours develop, patients may receive a further treatment with immunocytokine therapy according to the invention, to remove the further tumour.

Figure 4:
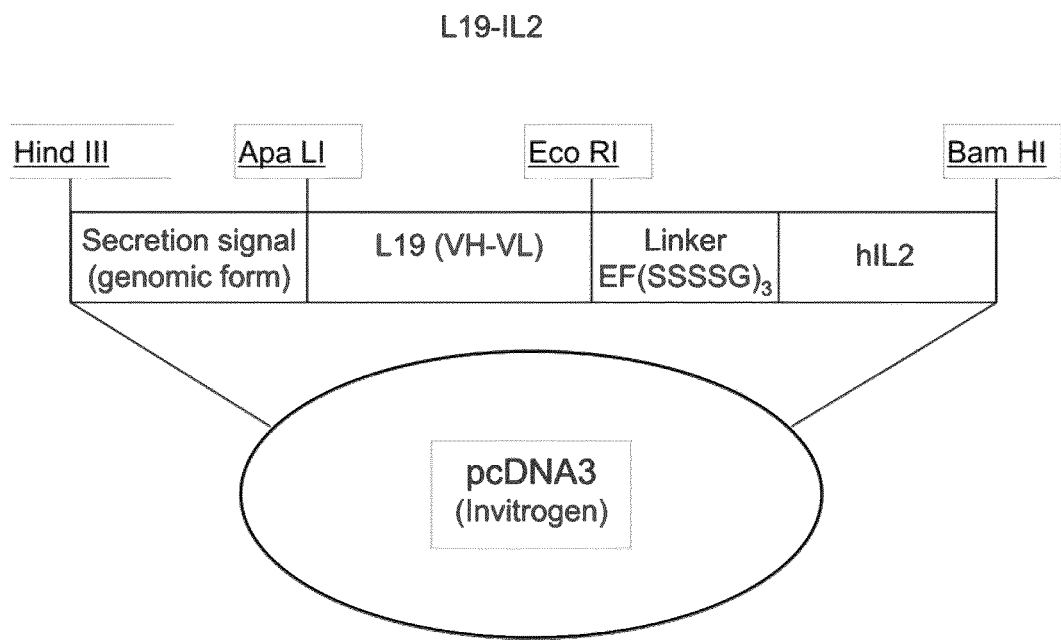
FIG. 4. Diagram of the cloning scheme for L19-IL2.

Nucleic acid molecules encoding the immunocytokines, and parts thereof, can be used in connection with the compositions and methods of the invention defined in the claims. The nucleic acid molecule may be a vector, e.g. a plasmid suitable for expression of the nucleotide sequence. Normally the nucleotide sequence is operably linked to a regulatory element such as a promoter for transcription. Exemplary vectors for the expression of L19-TNFα and L19-IL2 are disclosed in FIG. 3 and FIG. 4, respectively. The skilled person will appreciate that further DNA vectors capable for expressing the L19-TNFα and L19-IL2 immunocytokines of FIG. 1 and FIG. 2 can be readily constructed. Use of such DNA vectors are also within the scope of this invention when they are used in connection with the compositions and methods defined in the claims.

The nucleic acid molecules may be contained in a host cell, which may be a cell transfected with the nucleic acid molecules, or a daughter of such a cell. Cells, especially eukaryotic cells e.g. HEK and CHO cells, or bacterial cells e.g. *Escherichia coli*, containing the nucleic acid molecules can be used.

Immunocytokines of the invention may be produced using recombinant techniques, for example by expressing recombinant DNA encoding the immunocytokine in a cell. Normally the expression is performed in a eukaryotic host cell containing nucleic acid, as described above. Expression may therefore comprise culturing such a host cell. For L19-TNFα, trimerisation of the subunits may occur in the cell or during purification of the fusion proteins from the cell (21), (24).

Example 1: L19-TNFα Immunocytokine Formulations in Hepes Buffer

The following formulations were prepared to reach L19-TNFα concentration of 0.4 mg/ml. Formulations were obtained that allows higher concentrations of L19-TNFα to be produced and maintained without precipitation occurring.

The primary buffer component was Hepes, and the buffer pH, salt and polysorbate concentrations were varied.

Samples of each L19-TNFα formulation were stored at −80° C.±5° C. and subjected to multiple cycles of freezing and thawing. Three acceptance criteria were used to determine whether each buffer provides an acceptable L19-TNFα formulation:

1. Visual clarity=clear solution without visible particles,
2. A280 stability=less than 5% loss of 280 nm absorbance compared with original value, and
3. Trimer purity=over 95% purity, evaluated by size exclusion chromatography (SEC).

Hepes Buffers were Prepared at pH 7.5 and 8.0:

Hepes-1 comprises 30 mM Hepes at pH 7.5, 5 mM EDTA, 75 mM mannitol and 1.8% glycerol (w/v). None of the acceptance criteria were met.

Hepes-2 comprises 30 mM Hepes at pH 7.5, 5 mM EDTA, 75 mM mannitol, 1.8% glycerol (w/v) and 0.1% polysorbate20. None of the acceptance criteria were met.

Hepes-3 comprises 15 mM Hepes at pH 8.0, 5 mM EDTA, 75 mM mannitol and 1.8% glycerol (w/v). None of the acceptance criteria were met.

Hepes-4 comprises 15 mM Hepes at pH 8.0, 5 mM EDTA, 75 mM mannitol, 1.8% glycerol (w/v) and 0.005% polysorbate20. None of the acceptance criteria were met.

Hepes-5 comprises 15 mM Hepes at pH 8.0, 5 mM EDTA, 75 mM mannitol, 1.8% glycerol (w/v) and 0.01% polysorbate20. None of the acceptance criteria were met.

Hepes-6 comprises 15 mM Hepes at pH 8.0, 5 mM EDTA, 75 mM mannitol, 1.8% glycerol (w/v) and 0.05% polysorbate20. None of the acceptance criteria were met.

0.45 mg/mL, small particles appeared in the suspension and a visible pellet was recovered after centrifugation.

After concentrating the L19-TNFα immunocytokine solution in the Hepes-9 buffer, the product was stored at 2-8° C. and at −80° C. for 24 hours. In both cases small white particles were still visible in suspension. The 280 nm absorbance ($A_{280nm}$) of the solution was read after centrifugation and a 6%-8% of OD loss was recorded. Furthermore, when the product was filtered after storage at 2-8° C., a 16% of loss the $A_{280nm}$ reading was recorded, as shown in Table 1.

TABLE 1

| L19TNFα | | $A_{280\ nm}$ reading and visual appearance | | | |
|---|---|---|---|---|---|
| time-point | t = 0 | 0.562 | clear solution | | |
| | t = 24 hr 2-8° C. | 0.529 (−6%) | visible particles | →0.22 µm filtration 0.474 (−16%) | clear solution |
| | t = 24 hr −80° C. | 0.519 (−8%) | visible particles | | |

Hepes-7 comprises 15 mM Hepes at pH 8.0, 5 mM EDTA, 75 mM mannitol, 1.8% glycerol (w/v) and 0.1% polysorbate20. All three acceptance criteria were met.

Hepes-8 comprises 15 mM Hepes at pH 8.0, 5 mM EDTA, 75 mM mannitol, 1.8% glycerol (w/v) and 0.2% polysorbate20. All three acceptance criteria were met.

Further formulations were prepared to reach L19-TNFα concentration of 0.2 mg/ml:

Hepes-A comprises 30 mM Hepes at pH 7.5, 5 mM EDTA, 75 mM mannitol and 1.8% glycerol (w/v). None of the acceptance criteria were met.

Hepes-B comprises 15 mM Hepes at pH 8.0, 5 mM EDTA, 75 mM mannitol and 1.8% glycerol (w/v). None of the acceptance criteria were met.

Hepes-C comprises 15 mM Hepes at pH 8.0, 5 mM EDTA, 75 mM mannitol, 1.8% glycerol (w/v) and 0.1% polysorbate20. All three acceptance criteria were met.

Hepes-based formulations showed particles in suspension, which could only be dissolved in some cases by using 0.1% or 0.2% polysorbate20.

Following optimization, the most preferred hepes-based buffer for L19-TNFα was 15 mM Hepes, 75 mM Mannitol, 0.2% polysorbate20 (v/v), 1.8% Glycerol (w/v), 5 mM EDTA, pH 8.0—this buffer meets all three acceptance criteria and is denoted Hepes-9.

L19-TNFα was formulated in the Hepes-9 buffer at a final concentration of 0.092 mg/mL and was tested for stability. This L19-TNFα immunocytokine formulation was stored at −80° for up to 60 months during which time the protein concentration was monitored by measuring the 280 nm absorbance.

Figure 5:
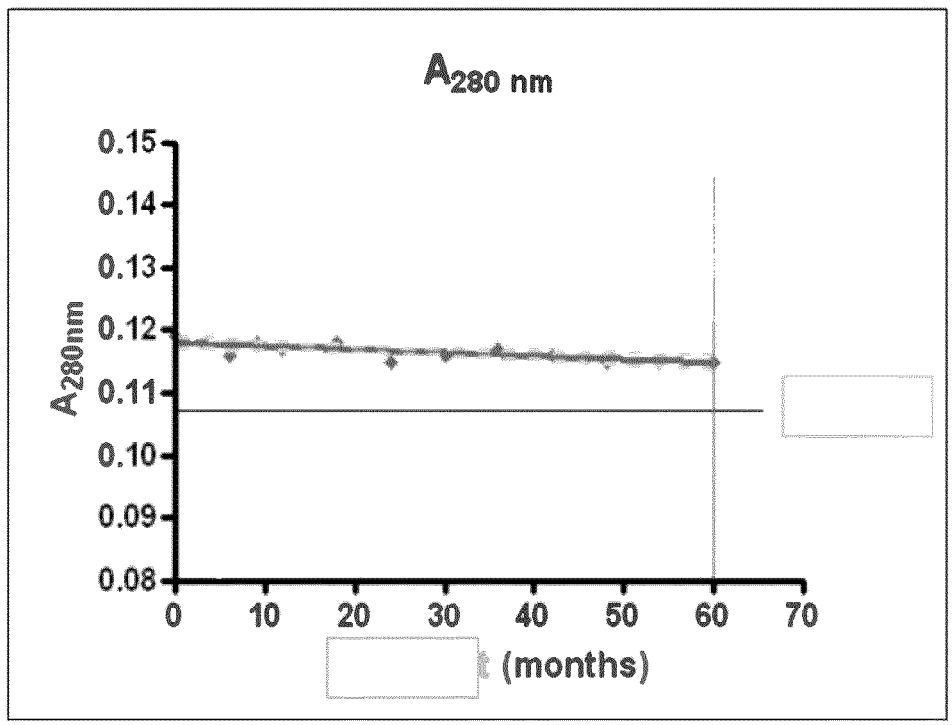
FIG. 5. Absorbance 280 nm of the L19-TNFα immunocytokine in the initial buffer solution at time points in months over a 60 month period. The horizontal line shows the lower detection limit.

FIG. 5 shows that the 280 nm absorbance does not decrease substantially over the 60 month period, indicating that the initial Hepes-9 buffer is suitable for long-term storage. The horizontal line shows the lower detection limit. The L19-TNFα immunocytokine is stable in the initial buffer stored at −80° for up to 60 months. 1 mg of L19-TNFα corresponds to approximately OD=1.3.

Example 2: Increased Concentration L19-TNFα Formulations

The Hepes-9 buffer described in Example 1 was not suitable for higher concentrations of L19-TNFα when starting from lower concentrations. For example, when the concentration was increased from 0.092 mg/mL up to 0.4-

Example 3: Identification of the Precipitate

To confirm that the loss of absorbance after concentration was actually due to a precipitation of L19-TNFα, we resuspended the pellet in solution and run a Western blotting, using an anti-TNFα antibody and a chemio-luminescent substrate.

Figure 6:
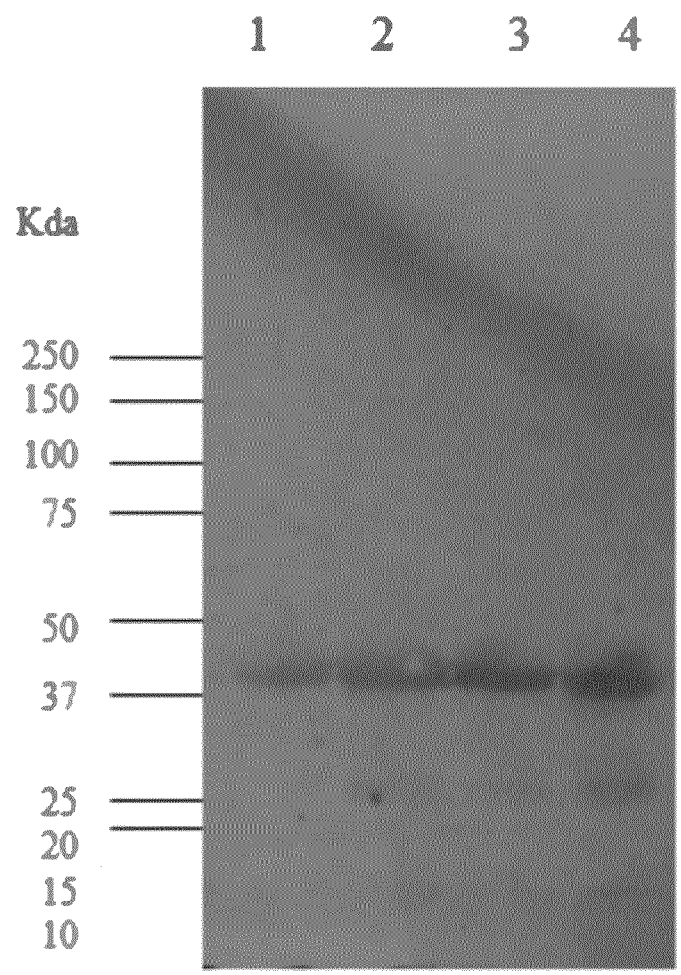
FIG. 6. Western Blot of precipitate arising from the initial L19-TNFα formulation, recovered by centrifugation to yield a pellet that was resuspended and run against dissolved L19-TNFα as a standard. Lane 1: L19-TNFα standard (reducing); lane 2: L19-TNFα standard (non-reducing); lane 3: L19-TNFα pellet (reducing); Lane 4: L19-TNFα pellet (non-reducing).
Figure 7:
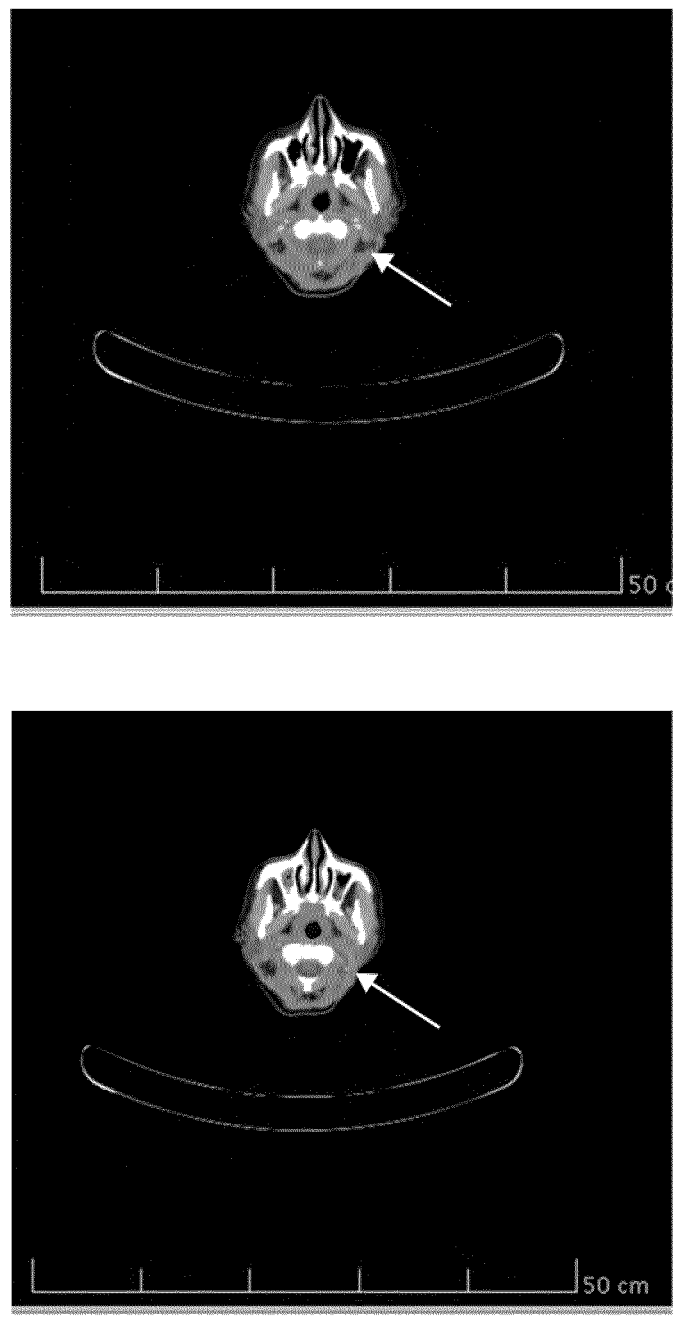
FIG. 7. Treatment of a patient with L19-TNFα in phosphate buffer in combination with L19-IL2. CT scan at Day 0 shows the presence of the melanoma lesion (top panel) and CT scan taken six months after the start of treatment, shows that the lesion has completely disappeared (lower panel).

FIG. 6 shows bands at the molecular weight of L19-TNFα both in the standard solution and in the pellet in both reducing and non-reducing conditions. This indicates that when the concentration of L19-TNFα in the Hepes-9 buffer is increased, the protein precipitates. Lane 1: L19-TNFα standard (reducing); lane 2: L19-TNFα standard (non-reducing); lane 3: L19-TNFα pellet (reducing); Lane 4: L19-TNFα pellet (non-reducing).

Example 4: Various L19-TNFα Immunocytokine Formulations

The following formulations were prepared to reach L19-TNFα concentration of 0.4 mg/ml. Formulations were obtained that allows higher concentrations of L19-TNFα to be produced and maintained without precipitation occurring.

The primary buffer component, buffer pH, salt and polysorbate concentrations were varied.

Samples of each L19-TNFα formulation were stored at −80° C.±5° C. and subjected to multiple cycles of freezing and thawing. Three acceptance criteria were used to determine whether each buffer provides an acceptable L19-TNFα formulation:
1. Visual clarity=clear solution without visible particles,
2. A280 stability=less than 5% loss of 280 nm absorbance compared with original value, and
3. Trimer purity=over 95% purity, evaluated by size exclusion chromatography (SEC).

Tris-Based Buffers were Prepared at pH 8.0 and 8.5:

Tris-1 comprises 15 mM Tris at pH 8.0 with 75 mM mannitol and 30 mM NaCl. None of the acceptance criteria were met.

Tris-2 comprises 15 mM Tris at pH 8.0, 75 mM mannitol, 30 mM NaCl and 1% glycerol (w/v). None of the acceptance criteria were met.

Tris-3 comprises 15 mM Tris at pH 8.5 and 75 mM mannitol and 30 mM NaCl. None of the acceptance criteria were met.

Tris-4 comprises 15 mM Tris at pH 8.5, 75 mM mannitol, 30 mM NaCl and 1% glycerol (w/v). None of the acceptance criteria were met.

Acetate Buffers were Prepared at pH 5:

Acetate-1 comprises 20 mM NaAc at pH 5.0, 8.5% Sucrose (w/v), 130 µM EDTA. None of the acceptance criteria were met.

Acetate-2 comprises 20 mM NaAc at pH 5.0, 8.5% Sucrose (w/v), 130 µM EDTA, 0.1% polysorbate20. None of the acceptance criteria were met.

Histidine Buffers were Prepared at pH 6, 8 and 9:

Hist-1 comprises 20 mM histidine at pH 6.0, 8.5% Sucrose (w/v), 130 µM EDTA. None of the acceptance criteria were met.

Hist-2 comprises 20 mM histidine at pH 8.0, 8.5% Sucrose (w/v), 130 µM EDTA. None of the acceptance criteria were met.

Hist-3 comprises 20 mM histidine at pH 9.0, 8.5% Sucrose (w/v), 130 µM EDTA. None of the acceptance criteria were met.

Citrate Buffer was Prepared at pH 6.6

Citrate-1 comprises 5.6 g/L sodium Citrate, 0.21 g/L citric acid, 70 g/L trehalose dihydrate, 0.2 g/L polysorbate80, 1% (w/v) glycerol, 5 mM EDTA, pH 6.6. Both the visual clarity and A280 stability criteria were met but the trimer purity criteria was not met indicating particles in suspension or aggregation of the trimer.

Borate Buffer was Prepared at pH 7.4

Borate-1 comprises 1.1 g/L sodium borate, 3.5 g/L boric acid, 55 mM mannitol, 1% (w/v) glycerol, 5 mM EDTA, pH 7.4. None of the acceptance criteria were met.

Carbonate Buffer was Prepared at pH 7.0 and pH 8.0

Carbonate-1 comprises 0.42% (w/v) $Na_2CO_3$, 5% Glucose, 0.9% (w/v) NaCl, 1% (w/v) glycerol, 1.5 mM KCl, 5 mM EDTA, pH 7.0. None of the acceptance criteria were met.

Carbonate-2 comprises 0.42% (w/v) $Na_2CO_3$, 5% Glucose, 0.9% (w/v) NaCl, 1% (w/v) glycerol, 1.5 mM KCl, 5 mM EDTA, pH 8.0. None of the acceptance criteria were met.

All tris, acetate, histidine, citrate, borate and carbonate-based buffers that were tested showed particles in suspension and were not considered for further investigation.

Example 5: L19-TNFα Immunocytokine Formulations in Phosphate Buffer

Phosphate buffers were then investigated. Again, samples were prepared to reach L19-TNFα concentration of 0.4 mg/ml. Samples were stored at −80° C.±5° C. and subjected to multiple cycles of freezing and thawing.

Phosphate Buffers were Prepared at pH 6.3, 6.5, 7.0 and 8.0 Using Monobasic Sodium Phosphate, with and without Dibasic Sodium Phosphate:

Phos-1 comprises 10 mM $NaH_2PO_4$ at pH 6.5, 50 mM mannitol, 1% glycerol (w/v) and 1.5 mM KCl. None of the acceptance criteria were met.

Phos-2 comprises 10 mM $NaH_2PO_4$ at pH 7.0, 50 mM mannitol, 1% glycerol (w/v) and 1.5 mM KCl. None of the acceptance criteria were met.

Phos-3 comprises 10 mM $NaH_2PO_4$ at pH 7.0, 50 mM mannitol, 1% glycerol (w/v), 1.5 mM KCl and 0.05% polysorbate20. None of the acceptance criteria were met.

Phos-4 comprises 10 mM $NaH_2PO_4$ at pH 7.0, 50 mM mannitol, 1% glycerol (w/v), 1.5 mM KCl, 20 mM NaCl and 0.05% polysorbate20. Neither the visual clarity nor the A280 stability criteria were met but the trimer purity criteria was met.

Phos-5 comprises 10 mM $NaH_2PO_4$ at pH 7.0, 50 mM mannitol, 1% glycerol (w/v), 1.5 mM KCl and 0.2% polysorbate20. Both the visual clarity and A280 stability criteria were met but the trimer purity criteria was not met.

Phos-6 comprises 10 mM $NaH_2PO_4$ at pH 7.0, 50 mM mannitol, 1% glycerol (w/v), 1.5 mM KCl, 20 mM NaCl and 0.2% polysorbate20. Both the visual clarity and A280 stability criteria were met but the trimer purity criteria was not met.

Phos-7 comprises 15 mM $NaH_2PO_4$ and 10 mM $Na_2HPO_4$ at pH 8.0, 75 mM mannitol, 1.5 mM KCl and 30 mM NaCl. None of the acceptance criteria were met.

Phos-8 comprises 10 mM $NaH_2PO_4$ at pH 8.0, 50 mM mannitol, 1% glycerol (w/v), 1.5 mM KCl and 0.05% polysorbate20. None of the acceptance criteria were met.

Phos-9 comprises 10 mM $NaH_2PO_4$ at pH 8.0, 50 mM mannitol, 1% glycerol (w/v), 1.5 mM KCl, 20 mM NaCl and 0.01% polysorbate20. All of the acceptance criteria were met.

Phos-10 comprises 10 mM $NaH_2PO_4$ at pH 8.0, 50 mM mannitol, 1% glycerol (w/v), 1.5 mM KCl, 20 mM NaCl and 0.02% polysorbate20. Both the trimer purity and A280 stability criteria were met but the visual clarity criteria was not met.

Phos-11 comprises 10 mM $NaH_2PO_4$ at pH 8.0, 50 mM mannitol, 1% glycerol (w/v), 1.5 mM KCl, 20 mM NaCl and 0.03% polysorbate20. Both the trimer purity and A280 stability criteria were met but the visual clarity criteria was not met.

Phos-12 comprises 10 mM $NaH_2PO_4$ at pH 8.0, 50 mM mannitol, 1% glycerol (w/v), 1.5 mM KCl, 20 mM NaCl and 0.2% polysorbate20. Both the visual clarity and A280 stability criteria were met but the trimer purity criteria was not met.

Phos-13 comprises 10 mM $NaH_2PO_4$ at pH 8.0, 50 mM mannitol, 1% glycerol (w/v), 1.5 mM KCl, 20 mM NaCl and 0.05% polysorbate20. None of the acceptance criteria were met.

Phos-14 comprises 10 mM $NaH_2PO_4$ at pH 8.0, 50 mM mannitol, 1% glycerol (w/v), 1.5 mM KCl and 0.2% polysorbate20. Both the visual clarity and A280 stability criteria were met but the trimer purity criteria was not met.

Phos-15 comprises 15 mM $NaH_2PO_4$ and 10 mM $Na_2HPO_4$ at pH 8.0, 75 mM mannitol, 1.5 mM KCl, 30 mM NaCl and 0.01% polysorbate20. Both the visual clarity and trimer purity criteria were met but the A280 stability criteria was not met.

Phos-16 comprises 15 mM $NaH_2PO_4$ and 10 mM $Na_2HPO_4$ at pH 8.0, 50 mM mannitol, 1.5% glycerol (w/v), 1.5 mM KCl, 10 mM NaCl and 0.01% polysorbate20. Both the visual clarity and A280 stability criteria were met but the trimer purity criteria was not met.

Phos-17 comprises 15 mM $NaH_2PO_4$ and 10 mM $Na_2HPO_4$ at pH 8.0, 50 mM mannitol, 1% glycerol (w/v), 1.5 mM KCl, 10 mM NaCl and 0.01% polysorbate20. Both the visual clarity and A280 stability criteria were met but the trimer purity criteria was not met.

Phos-18 comprises 15 mM $NaH_2PO_4$ and 10 mM $Na_2HPO_4$ at pH 8.0, 100 mM mannitol, 1% glycerol (w/v), 1.5 mM KCl, 30 mM NaCl and 0.01% polysorbate20. All of the acceptance criteria were met.

Phos-19 comprises 15 mM $NaH_2PO_4$ and 10 mM $Na_2HPO_4$ at pH 8.0, 75 mM mannitol, 1% glycerol (w/v), 1.5 mM KCl, 30 mM NaCl and 0.01% polysorbate20. All of the acceptance criteria were met.

Phos-20 comprises 15 mM $NaH_2PO_4$ and 10 mM $Na_2HPO_4$ at pH 8.0, 50 mM mannitol, 1% glycerol (w/v), 1.5 mM KCl, 10 mM NaCl and 0.01% polysorbate20. Both the visual clarity and A280 stability criteria were met but the trimer purity criteria was not met.

Phos-21 comprises 15 mM $NaH_2PO_4$ and 10 mM $Na_2HPO_4$ at pH 8.0, 75 mM mannitol, 1% glycerol (w/v), 1.5 mM KCl, 30 mM NaCl, 0.01% polysorbate20 and 5 mM EDTA. All three acceptance criteria were met.

Phos-22 comprises 15 mM $NaH_2PO_4$ and 10 mM $Na_2HPO_4$ at pH 8.0, 75 mM saccharose, 1.5 mM KCl, 30 mM NaCl, 1% (w/v) glycerol, 0.01% (v/v) polysorbate20 and 5 mM EDTA. All three acceptance criteria were met.

Phos-23 comprises 15 mM $NaH_2PO_4$ and 10 mM $Na_2HPO_4$ at pH 8.0, 70 g/L trehalose dihydrate (i.e. 185 mM trehalose), 1.5 mM KCl, 30 mM NaCl, 1% (w/v) glycerol, 0.01% (v/v) polysorbate20 and 5 mM EDTA. All three acceptance criteria were met.

Phos-24 comprises 15 mM $NaH_2PO_4$ and 10 mM $Na_2HPO_4$ at pH 8.0, 75 mM mannitol, 1.5 mM KCl, 30 mM NaCl, 1% (w/v) glycerol, 0.01% polysorbate80 and 5 mM EDTA. All three acceptance criteria were met.

Phos-25 comprises 15 mM $NaH_2PO_4$ and 10 mM $Na_2HPO_4$ at pH 8.0, 75 mM mannitol, 1.5 mM KCl, 30 mM NaCl, 1% (w/v) glycerol, 0.02% (w/v) polyoxyl 35 castor oil and 5 mM EDTA. None of the acceptance criteria were met.

Phos-26 comprises 6.7 mM $Na_2HPO_4$ at pH 6.3, 133 mM mannitol, 1.8 mM KCl, 20 mM NaCl and EDTA 5 mM. Phos-26 is a comparative example, based on a prior art buffer that was denoted "PBS-Siena" in WO2007/128563 (27). None of the acceptance criteria were met.

Phos-27 comprises 15 mM $NaH_2PO_4$ and 10 mM $Na_2HPO_4$ at pH 8.0, 75 mM mannitol, 1% glycerol (w/v), 1.5 mM KCl, 30 mM NaCl and 0.03% polysorbate20. All of the acceptance criteria were met.

Most preferably all three of the acceptance criteria are met.

The tests using e.g. Phos-22 and Phos-23 show that, regardless of the type of stabilizer, high quality soluble L19-TNFα solutions can be maintained.

Reduction of L19-TNFα concentration in each buffer has not been observed to reduce formulation stability.

The most preferred buffers selected for ongoing clinical tests were Phos-19 and Phos-21. The difference between these buffers is the presence of EDTA in Phos-21 and the absence of EDTA in Phos-19. While the presence or absence of EDTA is not observed to impact the solubility of L19-TNFα, nor the stability of the L19-TNFα solution, EDTA may be helpful as a preservative.

The importance of KCL was further investigated. Phos-19 Phosphate buffer was prepared without KCl as follows.

Phos-28 comprises 15 mM $NaH_2PO_4$ and 10 mM $Na_2HPO_4$ at pH 8.0, 75 mM mannitol, 1% glycerol (w/v), 30 mM NaCl and 0.01% polysorbate20. All of the acceptance criteria were met.

It was found that KCl was not essential in the formulation. A KCl concentration in the range about 1.5-1.8 mM helped to maintain the isotonicity of the solution by preventing a sudden pH shift during freezing of the formulation.

It was found that in absence of polysorbate the samples were not stable (e.g. Phos-26, borate-1 or Phos-25). (In Phos-25 polysorbate is replaced with the surfactant, polyoxyl 35 castor oil.)

Example 6: Effect of the pH on Phos-19 Phosphate Buffer

Phosphate buffer Phos-19 was further investigated regarding the pH. Phosphate buffer Phos-19 was prepared at pH 6.5, 7.0, 7.5, 7.8, 8.5, 8.8 and 9.0.

Phos-29 comprises 15 mM $NaH_2PO_4$ and 10 mM $Na_2HPO_4$ at pH 6.5, 75 mM mannitol, 1% glycerol (w/v), 1.5 mM KCl, 30 mM NaCl and 0.01% polysorbate20. None of the acceptance criteria were met.

Phos-30 comprises 15 mM $NaH_2PO_4$ and 10 mM $Na_2HPO_4$ at pH 7.0, 75 mM mannitol, 1% glycerol (w/v), 1.5 mM KCl, 30 mM NaCl and 0.01% polysorbate20. None of the acceptance criteria were met.

Phos-31 comprises 15 mM $NaH_2PO_4$ and 10 mM $Na_2HPO_4$ at pH 7.5, 75 mM mannitol, 1% glycerol (w/v), 1.5 mM KCl, 30 mM NaCl and 0.01% polysorbate20. None of the acceptance criteria were met.

Phos-32 comprises 15 mM $NaH_2PO_4$ and 10 mM $Na_2HPO_4$ at pH 7.8, 75 mM mannitol, 1% glycerol (w/v), 1.5 mM KCl, 30 mM NaCl and 0.01% polysorbate20. All of the acceptance criteria were met.

Phos-33 comprises 15 mM $NaH_2PO_4$ and 10 mM $Na_2HPO_4$ at pH 8.5, 75 mM mannitol, 1% glycerol (w/v), 1.5 mM KCl, 30 mM NaCl and 0.01% polysorbate20. All of the acceptance criteria were met.

Phos-34 comprises 15 mM $NaH_2PO_4$ and 10 mM $Na_2HPO_4$ at pH 8.8, 75 mM mannitol, 1% glycerol (w/v), 1.5 mM KCl, 30 mM NaCl and 0.01% polysorbate20. All of the acceptance criteria were met Phos-35 comprises 15 mM $NaH_2PO_4$ and 10 mM $Na_2HPO_4$ at pH 9.0, 75 mM mannitol, 1% glycerol (w/v), 1.5 mM KCl, 30 mM NaCl and 0.01% polysorbate20. None of the acceptance criteria were met.

It was therefore found that only pH values above 7.5 and below 9 are suitable for phosphate buffer formulations Example 7: Studies on the Salt and the Phosphate Concentration in the Phos-19 Phosphate Buffer The salt NaCl was substituted by another salt (e.g. KCl). Nacl was removed from Phos-19 and substituted by KCl at a concentration of 1.5 mM or 30 mM.

Phos-36 comprises 15 mM $NaH_2PO_4$ and 10 mM $Na_2HPO_4$ at pH 8.0, 75 mM mannitol, 1% glycerol (w/v), 1.5 mM KCl and 0.01% polysorbate20. All of the acceptance criteria were met.

Phos-37 comprises 15 mM $NaH_2PO_4$ and 10 mM $Na_2HPO_4$ at pH 8.0, 75 mM mannitol, 1% glycerol (w/v), 30 mM KCl and 0.01% polysorbate20. All of the acceptance criteria were met.

It was therefore demonstrated that different salts can be used in phosphate buffer formulations.

Phosphate buffer (Phos-19 variants) comprising various concentrations of $NaH_2PO_4$ and $Na_2HPO_4$ were tested.

Phos-38 comprises 10 mM NaH2PO4 and 10 mM Na2HPO4 at pH 8.0, 75 mM mannitol, 1% glycerol (w/v), 1.5 mM KCl, 30 mM NaCl and 0.01% polysorbate20. All of the acceptance criteria were met.

Phos-39 comprises 20 mM NaH2PO4 and 10 mM Na2HPO4 at pH 8.0, 75 mM mannitol, 1% glycerol (w/v), 1.5 mM KCl, 30 mM NaCl and 0.01% polysorbate20. All of the acceptance criteria were met.

Phos-40 comprises 15 mM NaH2PO4 and 15 mM Na2HPO4 at pH 8.0, 75 mM mannitol, 1% glycerol (w/v), 1.5 mM KCl, 30 mM NaCl and 0.01% polysorbate20. All of the acceptance criteria were met.

Example 8: Further Studies on Phosphate Buffers, Regarding Glycerol, KCl, and Tween80

Further investigations using the Phos-28 (15 mM $NaH_2PO_4$ and 10 mM $Na_2HPO_4$ at pH 8.0, 75 mM mannitol, 1% glycerol (w/v), 30 mM NaCl and 0.01% polysorbate20) were done. Phos-28 corresponds to Phos-19 without KCl.

(i) Various concentrations of glycerol (w/v) were tested: Glycerol concentrations of 0.5% and 1.5% (w/v) were tested.

Phos-41 comprises 15 mM $NaH_2PO_4$ and 10 mM $Na_2HPO_4$ at pH 8.0, 75 mM mannitol, 0.5% glycerol (w/v), 30 mM NaCl and 0.01% polysorbate20. All of the acceptance criteria were met.

Phos-42 comprises 15 mM $NaH_2PO_4$ and 10 mM $Na_2HPO_4$ at pH 8.0, 75 mM mannitol, 1.5% glycerol (w/v), 30 mM NaCl and 0.01% polysorbate20. All of the acceptance criteria were met.

It was therefore found that a concentration of glycerol as low as 0.5% can be used in phosphate buffer formulations that pass all three acceptance criteria.

Example 9: Combining L19-TNFα and L19-IL2 Formulations

It was then investigated if the new formulation buffer of L19-TNFα dissolved in Phos-19 was suitable for combination with L19-IL2 in the clinical setting.

Various mixes of L19-TNFα in the Phos-19 buffer were performed with L19-IL2 in a buffer comprising 6.7 mM $NaH_2PO_4$, 20 mM NaCl, 1.8 mM KCl, 133 mM mannitol, 0.1% polysorbate80 (v/v), 1% glycerol (w/v) and 5 mM EDTA and has pH 6.3. These formulations were mixed together and the resultant mixtures were tested both at time 0 and after 3 hours at room temperature. We considered that in the clinical operations, the mixture would in no case exceed 3 hours of incubation as the two products are mixed and injected almost immediately. The mixtures were prepared by adding L19-TNFα into the L19-IL2 solution and vice versa. The results are shown in Table 2.

TABLE 2

| Time point | Sample | Calculated Protein Amount § | Osmolality mOsmol/Kg | pH | % IR | TNFα Bioactivity * | IL2 Bioactivity * | SDS PAGE |
|---|---|---|---|---|---|---|---|---|
| t = 0 | Mix 1 0.4 mg L19TNFa + 2.17 mg L19IL2 | L19TNFa: 0.46 mg L19IL2: 2.18 mg | 336 | 7.24 | >99% | 95% | 94% | L19TNFa and L19IL2 band visible |
|  | Mix 2 2.17 mg L19IL2 + 0.4 mg L19TNFa | L19IL2: 2.11 mg L19TNFa: 0.45 mg | 329 | 7.36 | >99% | 116% | 90% | L19TNFa and L19IL2 band visible |
| t = 3 hr RT | Mix1 0.4 mg L19TNFa + 2.17 mg L19IL2 | L19TNFa: 0.42 mg L19IL2: 2.07 mg | n/a | n/a | >99% | 109% | 89% | L19TNFa and L19IL2 band visible |
|  | Mix 2 2.17 mg L19IL2 + 0.4 mg L19TNFa | L19IL2: 2.18 mg L19TNFa: 0.45 mg | n/a | n/a | >99% | 112% | 86% | L19TNFa and L19IL2 band visible |

(ii) Various Concentrations of Tween80:

Phosphate buffer (Phos-28) comprising various concentrations of Tween80 instead of Tween20 were tested.

Phos-43 comprises 15 mM $NaH_2PO_4$ and 10 mM $Na_2HPO_4$ at pH 8.0, 75 mM mannitol, 1% glycerol (w/v), 30 mM NaCl and 0.005% polysorbate80. All of the acceptance criteria were met.

Phos-44 comprises 15 mM $NaH_2PO_4$ and 10 mM $Na_2HPO_4$ at pH 8.0, 75 mM mannitol, 1% glycerol (w/v), 30 mM NaCl and 0.03% polysorbate80. All of the acceptance criteria were met.

Phos-45 comprises 15 mM $NaH_2PO_4$ and 10 mM $Na_2HPO_4$ at pH 8.0, 75 mM mannitol, 1% glycerol (w/v), 30 mM NaCl and 0.1% polysorbate80. All of the acceptance criteria were met.

It was therefore found that a concentration of polysorbate 80 as low as 0.005% can be used for phosphate buffer formulations.

§ Protein amount was calculated by quantitative Cation Exchange chromatography. Bioactivity was calculated by referring to TNFα or IL2 standard. IR=Immunoreactivity Importantly, a clear solution with no protein loss or aggregates was recovered after the 3 hours. Overall the mixture was found to be stable.

Example 10: Treatment of a Patient with L19-TNFα in Phosphate Buffer in Combination with L19-IL2

The new formulation of L19-TNFα dissolved in Phos-21 in combination with L19-IL2, which is in a buffer comprising 6.7 mM $NaH_2PO_4$, 20 mM NaCl, 1.8 mM KCl, 133 mM mannitol, 0.28% polysorbate80 (v/v), and 1% glycerol (w/v) and which has pH 6.3, was then tested in a clinical setting.

A 59 year old patient was diagnosed with Stage IIIB melanoma and presented an injectable retroauricolar metastasis.

The patient received four treatments through intralesional injection with L19-TNFα dissolved in Phos-21 in combination with L19-IL2. First and second treatments consisted of a dose of 13 Mio IU of L19IL2 and 400 µg of L19-TNFα. The third was ¾ of the dose of L19-TNFα and L19-IL2 and the fourth treatment was ½ of the dose of L19-TNFα and L19-IL2.

Results

The CT scan at Day 0 shows the presence of the melanoma lesion (FIG. 5, top panel). The CT scan taken six months after the start of treatment, shows that the lesion has completely disappeared (FIG. 5, lower panel).

Example 11: Treatment of a Patient Having a Sarcoma with L19-TNFα in Phosphate Buffer in Combination with Doxorubicin A patient with chondrosarcoma was treated with 2 cycles of L19-TNFα (17 ug/kg-3 weekly injections per cycle) and doxorubicin (60 mg/m² 1 weekly injection per cycle), administered by infusion.

The target lesion in lung showed growth stabilization at CT after 2 cycles of treatment (FIG. 8).

SEQUENCES

SEQ ID NO: 1 = L19-TNFα
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSGDGSSGGSGGASEIVLTQSPGTLSLSPGERATLS
CRASQSVSSSFLAWYQQKPGQAPRLLIYYASSRATGIPDRFSGSGSGTDF
TLTISRLEPEDFAVYYCQQTGRIPPTFGQGTKVEIKEFSSSSGSSSSGSS
SSGVRSSSRTPSDKPVAHVVANPQAEGQLQWLNRRANALLANGVELRDNQ
LVVPSEGLYLIYSQVLFKGQGCPSTHVLLTHTISRIAVSYQTKVNLLSAI
KSPCQRETPEGAEAKPWYEPIYLGGVFQLEKGDRLSAEINRPDYLDFAES
GQVYFGIIAL

SEQ ID NO: 2 = L19-IL2
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSGDGSSGGSGGASEIVLTQSPGTLSLSPGERATLS
CRASQSVSSSFLAWYQQKPGQAPRLLIYYASSRATGIPDRFSGSGSGTDF
TLTISRLEPEDFAVYYCQQTGRIPPTFGQGTKVEIKEFSSSSGSSSSGSS
SSGAPTSSSTKKTQLQLEHLLLDLQMILNGINNYKNPKLTRMLTFKFYMP
KKATELKHLQCLEEELKPLEEVLNLAQSKNFHLRPRDLISNINVIVLELK
GSETTFMCEYADETATIVEFLNRWITFCQSIISTLT

REFERENCES

All publications, patent and patent applications cited herein or filed with this application, including references filed as part of an Information Disclosure Statement are incorporated by reference in their entirety.

1. Testori A, Faries M B, Thompson J F, Pennacchioli E, Deroose J P, van Geel A N, Verhoef C, Verrecchia F, Soteldo J (2011) Local and intralesional therapy of in-transit melanoma metastases. J Surg Oncol 104 (4):391-396. doi: 10.1002/jso.22029
2. Si Z, Hersey P, Coates A S (1996) Clinical responses and lymphoid infiltrates in metastatic melanoma following treatment with intralesional GM-CSF. Melanoma Res 6 (3):247-255.
3. von Wussow P, Block B, Hartmann F, Deicher H (1988) Intralesional interferon-alpha therapy in advanced malignant melanoma. Cancer 61 (6):1071-1074.
4. Kubo H, Ashida A, Matsumoto K, Kageshita T, Yamamoto A, Saida T (2008) Interferon-beta therapy for malignant melanoma: the dose is crucial for inhibition of proliferation and induction of apoptosis of melanoma cells. Arch Dermatol Res 300 (6):297-301. doi: 10.1007/s00403-008-0841-6
5. Gutwald J G, Groth W, Mahrle G (1994) Peritumoral injections of interleukin 2 induce tumour regression in metastatic malignant melanoma. Br J Dermatol 130 (4): 541-542.
6. Radny P, Caroli U M, Bauer J, Paul T, Schlegel C, Eigentler T K, Weide B, Schwarz M, Garbe C (2003) Phase II trial of intralesional therapy with interleukin-2 in soft-tissue melanoma metastases. Br J Cancer 89 (9): 1620-1626. doi: 10.1038/sj.bjc.6601320
7. Weide B, Derhovanessian E, Pflugfelder A, Eigentler T K, Radny P, Zelba H, Pfohler C, Pawelec G, Garbe C (2010) High response rate after intratumoral treatment with interleukin-2: results from a phase 2 study in 51 patients with metastasized melanoma. Cancer 116 (17):4139-4146. doi: 10.1002/cncr.25156
8. Boyd K U, Wehrli B M, Temple C L (2011) Intra-lesional interleukin-2 for the treatment of in-transit melanoma. J Surg Oncol 104 (7):711-717. doi: 10.1002/jso.21968
9. Dehesa L A, Vilar-Alejo J, Valeron-Almazan P, Carretero G (2009) Experience in the treatment of cutaneous in-transit melanoma metastases and satellitosis with intralesional interleukin-2. Actas Dermosifiliogr 100 (7):571-585.
10. Tartaglia L. A., et al (1993) Ligand Passing: The 75-kDa Tumor Necrosis Factor (TNF) Receptor Recruits TNF for Signaling by the 55-kDa TNF' Receptor. J. Biol. Chem., 268: 18542-18548.
11. Carswell E. A., et al, (1975) An endotoxin-induced serum factor that causes necrosis of tumors. Proc. Natl. Acad. Sci. USA, 72: 3666-3670,
12. Belson L., et al, (1975) Effect of tumour necrosis factor on cultured human melanoma cells. Nature, 258: 731-732.
13. Blick M. et al. (1987) Phase I Study of Recombinant Tumor Necrosis Factor in Cancer Patients Cancer Res. 47: 2989.
14. Franker D. L., et al, (1994) Isolated limb perfusion with high-dose tumor necrosis factor for extremity melanoma and sarcoma. Important Adv. Oncol. 179-192.
15. Clauss M., et al. (1990) A Polypeptide Factor Produced by Fibrosarcoma Cells That Induces Endothelial Tissue Factor and Enhances the Procoagulant Response to Tumor Necrosis Factor/Cachectin. J. Biol. Chem., 265: 7078-7083.
16. Clauss., et al. (1990) Vascular permeability factor: a tumor-derived polypeptide that induces endothelial cell and monocyte procoagulant activity, and promotes monocyte migration. J. Exp. Med., 172:1535-1545.
17. Palladino Jr. M. A., et al. (1987) Characterization of the antitumor activities of human tumor necrosis factor-alpha and the comparison with other cytokines: induction of tumor-specific immunity. J. Immunol., 138:4023-4032.
18. Pasche N, Neri D (2012) Immunocytokines: a novel class of potent armed antibodies. Drug Discov Today 17 (11-12):583-590. doi: 10.1016/j.drudis.2012.01.007
19. WO99/058570
20. Carnemolla B, Borsi L, Balza E et al. (2002) Enhancement of the antitumor properties of interleukin-2 by its targeted delivery to the tumor blood vessel extracellular matrix. Blood 99 (5):1659-1665. doi: 10.1182/blood.V99.5.1659
21. WO01/062298
22. Pretto F, Elia G, Castioni N, Neri D (2014) Preclinical evaluation of IL2-based immunocytokines supports their use in combination with dacarbazine, paclitaxel and TNF-based immunotherapy. Cancer Immunol Immunother 63 (9):901-910. doi: 10.1007/s00262-014-1562-7
23. Weide B, Eigentler T K, Pflugfelder A et al. (2014) Intralesional treatment of stage III metastatic melanoma patients with L19-IL2 results in sustained clinical and systemic immunologic responses. Cancer Immunol Res 2 (7):668-678. doi: 10.1158/2326-6066.CIR-13-0206
24. Danielli R., Patuzzo R., Di Giacomo A M. Et al., (2014) A phase II study of intratumoral application of L19L2/L19TNF in melanoma patients in clinical stage III or stage IV M1a with presence of injectable cutaneous and/or subcutaneous lesions. J Clin Oncol, 32 (5s) (Suppl; abstr TPS9103^)
25. WO13/045125
26. Weide et al. (2010) High response rate after intratumoral treatment with interleukin-2. Cancer 4139-4146.
27. WO2007/128563

The invention claimed is:

1. A composition comprising at least 0.4 mg/ml L19-TNFa as set forth in SEQ ID NO: 1, dissolved in a sodium phosphate buffer, which comprises NaCl at a concentration of at least 1.5 mM, polysorbate at a concentration of 0.005-0.1% (v/v), glycerol at a concentration of 0.5-1.5% w/v, and a stabilizer at a concentration of 65 mM-185 mM, wherein pH of the sodium phosphate buffer is higher than 7.5 and lower than 9.

2. The composition of claim 1, wherein the sodium phosphate buffer comprises $NaH_2PO_4$ at a concentration of 5-25 mM.

3. The composition of claim 1, wherein the sodium phosphate buffer comprises $Na_2HPO_4$ at a concentration of 5-20 mM.

4. The composition of claim 1, wherein the sodium phosphate buffer comprises KCl at a concentration of 1-2 mM.

5. The composition of claim 1, wherein the sodium phosphate buffer comprises EDTA at a concentration of 1-20 mM.

6. The composition of claim 1, wherein the stabilizer is a sugar.

7. The composition of claim 6, wherein the sugar is selected from the group consisting of mannitol, trehalose, sucrose, sorbitol, maltose and xylitol.

8. The composition of claim 7, wherein the sugar is mannitol.

9. The composition of claim 1, wherein the NaCl is at a concentration of 10-30 mM.

10. The composition of claim 1, wherein the sodium phosphate buffer comprises the polysorbate at a concentration of 0.005-0.03%.

11. The composition of claim 1, wherein the polysorbate is polysorbate20.

12. The composition of claim 1, wherein the composition is a clear solution without visible particles.

13. A kit comprising a first container comprising the composition of claim 1, and a second container comprising a preparation of an L19-IL2 immunocytokine.

14. The kit of claim 13, further comprising instructions to mix the L19-TNFα with the preparation of the L19-IL2 immunocytokine, and to administer resultant mixture to a cancer patient.

15. The kit of claim 13, wherein the preparation of the L19-IL2 comprises $NaH_2PO_4$ at a concentration of about 1-50 mM, NaCl at a concentration of about 1-50 mM, KCl at a concentration of about 1-2 mM, mannitol at a concentration of about 50-200 mM, polysorbate80 at a concentration of about 0.05-0.3% (v/v), and glycerol at a concentration of about 0.5-2%, and has pH of about 5.5-7.0.

16. A method of treating a solid cancer in a patient, comprising injecting the composition of claim 1 into a tumor or lesion of the patient, or by administering the composition of claim 1 to the patient by infusion.

17. The method of claim 16, wherein the solid cancer is a skin cancer or a sarcoma.

18. The method of claim 16, wherein the solid cancer is a primary tumor.

19. The method of claim 16, wherein the solid cancer is carcinoma.

20. The method of claim 16, further comprising, prior to the administering, mixing the composition of claim 1 with an L19-IL2 immunocytokine preparation.

21. The method of claim 20, wherein the L19-IL2 immunocytokine preparation comprises $NaH_2PO_4$ at a concentration of about 1-50 mM, NaCl at a concentration of about 1-50 mM, KCl at a concentration of about 1-2 mM, mannitol at a concentration of about 50-200 mM, polysorbate80 at a concentration of about 0.05-0.3% (v/v), and glycerol at a concentration of about 0.5-2%, and has pH of about 5.5-7.0.

22. The method of claim 16, wherein the injecting further comprises injecting doxorubicin.

* * * * *

SEQUENCE LISTING

```
<160> NUMBER OF SEQ ID NOS: 8

<210> SEQ ID NO 1
<211> LENGTH: 410
<212> TYPE: PRT
<213> ORGANISM: Artificial Sequence
<220> FEATURE:
<223> OTHER INFORMATION: L19-TNFalpha

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Glu Phe Ser Ser
225                 230                 235                 240

Ser Ser Gly Ser Ser Ser Ser Gly Ser Ser Ser Gly Val Arg Ser
                245                 250                 255

Ser Ser Arg Thr Pro Ser Asp Lys Pro Val Ala His Val Val Ala Asn
            260                 265                 270
```

```
Pro Gln Ala Glu Gly Gln Leu Gln Trp Leu Asn Arg Arg Ala Asn Ala
            275                 280                 285

Leu Leu Ala Asn Gly Val Glu Leu Arg Asp Asn Gln Leu Val Val Pro
        290                 295                 300

Ser Glu Gly Leu Tyr Leu Ile Tyr Ser Gln Val Leu Phe Lys Gly Gln
305                 310                 315                 320

Gly Cys Pro Ser Thr His Val Leu Leu Thr His Thr Ile Ser Arg Ile
                325                 330                 335

Ala Val Ser Tyr Gln Thr Lys Val Asn Leu Leu Ser Ala Ile Lys Ser
                340                 345                 350

Pro Cys Gln Arg Glu Thr Pro Glu Gly Ala Glu Ala Lys Pro Trp Tyr
            355                 360                 365

Glu Pro Ile Tyr Leu Gly Gly Val Phe Gln Leu Glu Lys Gly Asp Arg
        370                 375                 380

Leu Ser Ala Glu Ile Asn Arg Pro Asp Tyr Leu Asp Phe Ala Glu Ser
385                 390                 395                 400

Gly Gln Val Tyr Phe Gly Ile Ile Ala Leu
                405                 410

<210> SEQ ID NO 2
<211> LENGTH: 386
<212> TYPE: PRT
<213> ORGANISM: Artificial Sequence
<220> FEATURE:
<223> OTHER INFORMATION: L19-IL2

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220
```

Pro Thr Phe Gly Gln Gly Thr Lys Val Glu Ile Lys Glu Phe Ser Ser
225                 230                 235                 240

Ser Ser Gly Ser Ser Ser Gly Ser Ser Ser Gly Ala Pro Thr
            245                 250                 255

Ser Ser Ser Thr Lys Lys Thr Gln Leu Gln Leu Glu His Leu Leu Leu
            260                 265                 270

Asp Leu Gln Met Ile Leu Asn Gly Ile Asn Asn Tyr Lys Asn Pro Lys
            275                 280                 285

Leu Thr Arg Met Leu Thr Phe Lys Phe Tyr Met Pro Lys Lys Ala Thr
            290                 295                 300

Glu Leu Lys His Leu Gln Cys Leu Glu Glu Glu Leu Lys Pro Leu Glu
305                 310                 315                 320

Glu Val Leu Asn Leu Ala Gln Ser Lys Asn Phe His Leu Arg Pro Arg
                325                 330                 335

Asp Leu Ile Ser Asn Ile Asn Val Ile Val Leu Glu Leu Lys Gly Ser
                340                 345                 350

Glu Thr Thr Phe Met Cys Glu Tyr Ala Asp Glu Thr Ala Thr Ile Val
                355                 360                 365

Glu Phe Leu Asn Arg Trp Ile Thr Phe Cys Gln Ser Ile Ile Ser Thr
370                 375                 380

Leu Thr
385

<210> SEQ ID NO 3
<211> LENGTH: 116
<212> TYPE: PRT
<213> ORGANISM: Artificial Sequence
<220> FEATURE:
<223> OTHER INFORMATION: L19-VH

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 4
<211> LENGTH: 12
<212> TYPE: PRT
<213> ORGANISM: Artificial Sequence
<220> FEATURE:
<223> OTHER INFORMATION: scFV Linker

<400> SEQUENCE: 4

Gly Asp Gly Ser Ser Gly Gly Ser Gly Gly Ala Ser
1               5                   10

<210> SEQ ID NO 5
<211> LENGTH: 108
<212> TYPE: PRT
<213> ORGANISM: Artificial Sequence
<220> FEATURE:
<223> OTHER INFORMATION: L19-VL

<400> SEQUENCE: 5

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
            35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105
```

<210> SEQ ID NO 6
<211> LENGTH: 17
<212> TYPE: PRT
<213> ORGANISM: Artificial Sequence
<220> FEATURE:
<223> OTHER INFORMATION: Linker

<400> SEQUENCE: 6

```
Glu Phe Ser Ser Ser Ser Gly Ser Ser Ser Gly Ser Ser Ser Ser Ser
1               5                   10                  15

Gly
```

<210> SEQ ID NO 7
<211> LENGTH: 157
<212> TYPE: PRT
<213> ORGANISM: Artificial Sequence
<220> FEATURE:
<223> OTHER INFORMATION: hTNFalpha

<400> SEQUENCE: 7

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
```

-continued

```
                115                 120                 125
Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 8
<211> LENGTH: 133
<212> TYPE: PRT
<213> ORGANISM: Artificial Sequence
<220> FEATURE:
<223> OTHER INFORMATION: hIL2

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```